US012603146B2

(12) United States Patent
Guo et al.

(10) Patent No.: US 12,603,146 B2
(45) Date of Patent: Apr. 14, 2026

(54) MULTIMODAL DOMAIN EMBEDDINGS VIA CONTRASTIVE LEARNING

(71) Applicant: MICROSOFT TECHNOLOGY LICENSING, LLC, Redmond, WA (US)

(72) Inventors: Zhihui Guo, Kirkland, WA (US); Pramod Kumar Sharma, Seattle, WA (US); Liang Du, Redmond, WA (US); Robin Abraham, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1185 days.

(21) Appl. No.: 17/410,701

(22) Filed: Aug. 24, 2021

(65) Prior Publication Data

US 2023/0067528 A1     Mar. 2, 2023

(51) Int. Cl.
| | |
|---|---|
| *G01N 33/48* | (2006.01) |
| *G01N 33/50* | (2006.01) |
| *G06F 18/214* | (2023.01) |
| *G16B 15/00* | (2019.01) |
| *G16H 70/40* | (2018.01) |

(52) U.S. Cl.
CPC ......... *G16B 15/00* (2019.02); *G06F 18/2155* (2023.01); *G16H 70/40* (2018.01)

(58) Field of Classification Search
CPC .... G16B 15/00; G06F 18/2155; G16H 70/40; G06N 3/048; G06N 3/0455; G06N 3/088; G06N 3/0895; G16C 20/30; G16C 20/40; G16C 20/70
See application file for complete search history.

(56) References Cited

U.S. PATENT DOCUMENTS

| | | | |
|---|---|---|---|
| 2019/0096524 A1* | 3/2019 | Hu | G06N 20/00 |
| 2019/0287685 A1* | 9/2019 | Wu | G06F 40/295 |

OTHER PUBLICATIONS

Asada, et al., "Enhancing Drug-Drug Interaction Extraction from Texts by Molecular Structure Information", In Proceedings of the 56th Annual Meeting of The Association for Computational Linguistics, Jul. 15, 2018, pp. 680-685.

Fang, et al., "Knowledge-aware Contrastive Molecular Graph Learning", In Repository of arXiv:2103.13047v1, Mar. 24, 2021, 7 Pages.

(Continued)

*Primary Examiner* — Russell S Negin
(74) *Attorney, Agent, or Firm* — Workman Nydegger

(57)     ABSTRACT

Systems and methods are provided for building and training machine learning models configured to generate in-domain embeddings and perform multimodal analysis inside the same domain. The models include a first encoder trained to receive input from one or more entities represented in a first modality and to encode the one or more entities in the first modality, such that the first encoder is configured to output a first set of embeddings. The models also include a second encoder trained to receive input from one or more entities represented in the second modality and to encode the one or more entities in the second modality, such that the second encoder is configured to output a second set of embeddings. The models also include a projection layer configured to project the first set of embeddings and the second set of embeddings to a shared contrastive space.

20 Claims, 16 Drawing Sheets

(56)     References Cited

OTHER PUBLICATIONS

Guo, et al., "MM-Deacon: Multimodal Molecular Domain Embedding Analysis Via Contrastive Learning", Retrieved From: https://www.biorxiv.org/content/10.1101/2021.09.17.460864v1.full.pdf, Sep. 20, 2021, 21 Pages.

Guo, et al., "Multilingual Molecular Representation Learning via Contrastive Pre-training", In Proceedings of the 60th Annual Meeting of the Association for Computational Linguistics, May 1, 2022, pp. 3441-3453.

Koge, et al., "Embedding of Molecular Structure Using Molecular Hypergraph Variational Autoencoder with Metric Learning", In Journal of Molecular informatics, vol. 40, Issue 2, Nov. 8, 2020, 7 Pages.

Li, et al., "Learn Molecular Representations from Large-Scale Unlabeled Molecules for Drug Discovery", In Repository of arXiv:2012.11175v1, Dec. 21, 2020, 20 Pages.

Liu, et al., "Self-Supervised Learning: Generative or Contrastive", In Repository of arXiv:2006.08218v5, Mar. 20, 2021, 24 Pages.

"International Search Report and Written Opinion Issued in PCT Application No. PCT/US22/038109", Mailed Date: Dec. 23, 2022, 14 Pages.

Rahate, et al., "Multimodal Co-learning: Challenges, Applications with Datasets, Recent Advances and Future Directions", In Repository of arXiv:2107.13782v1, Jul. 29, 2021, 77 Pages.

Wang, et al., "MolCLR: Molecular Contrastive Learning of Representations via Graph Neural Networks", In Repository arXiv:2102.10056v1, Feb. 19, 2021, 14 Pages.

* cited by examiner

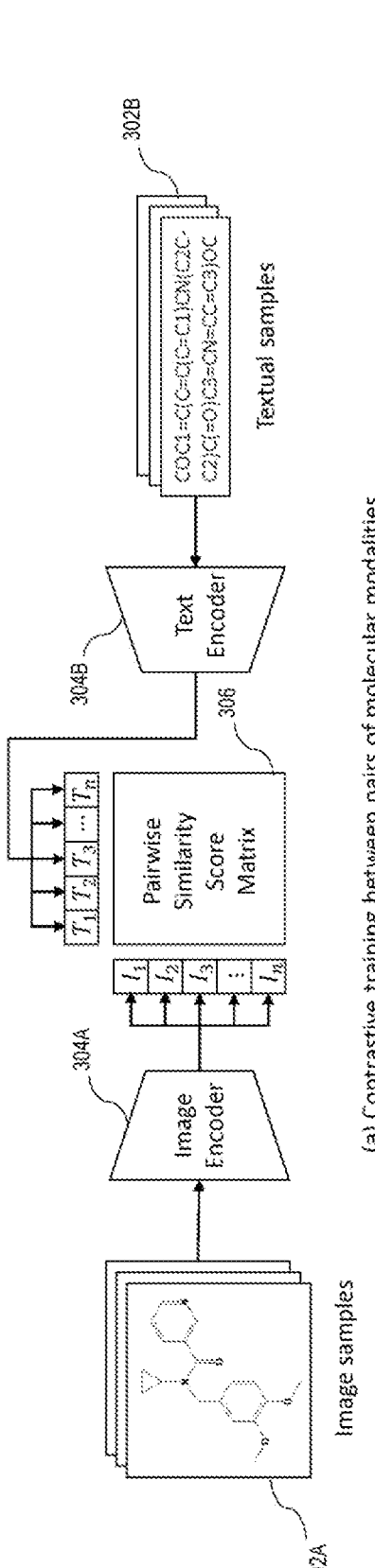
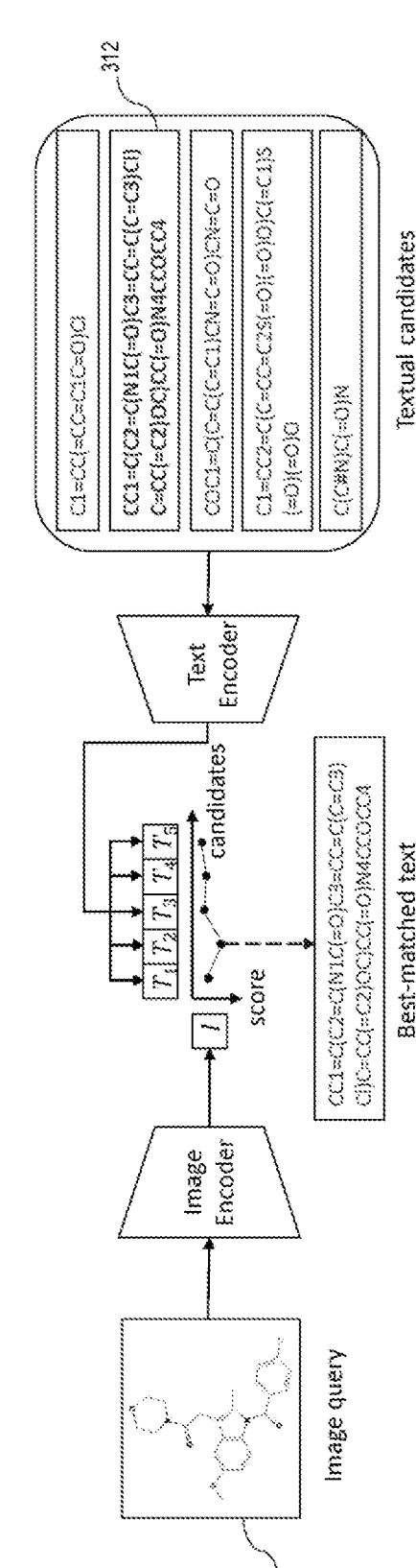
(a) Contrastive training between pairs of molecular modalities
(b) Zero-shot molecular image-to-text retrieval. Bold textual candidate is the ground truth
*FIG. 3*

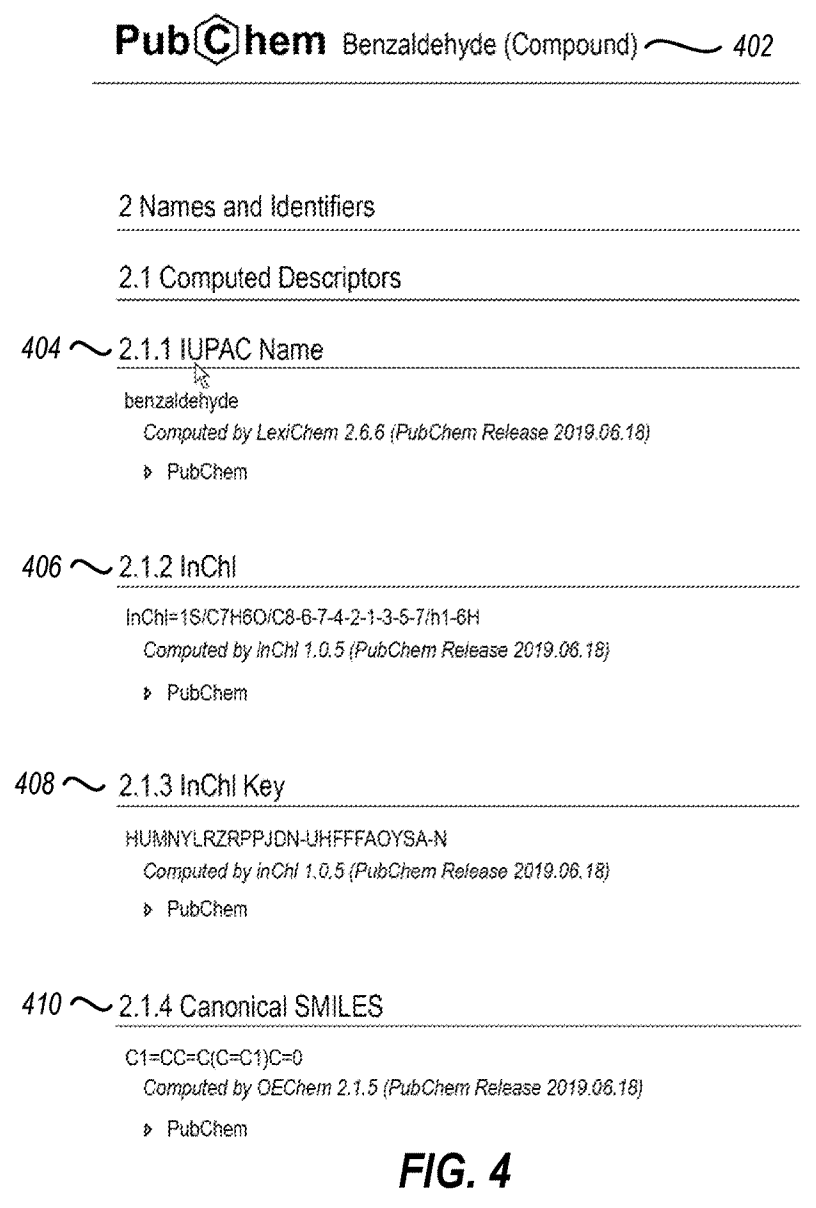

Pub⬡hem Benzaldehyde (Compound) ⟋ 402

2 Names and Identifiers 2.1 Computed Descriptors

404 ⟋ 2.1.1 IUPAC Name benzaldehyde
*Computed by LexiChem 2.6.6 (PubChem Release 2019.06.18)*

▷ PubChem

406 ⟋ 2.1.2 InChI

InChI=1S/C7H6O/c8-6-7-4-2-1-3-5-7/h1-6H
*Computed by InChI 1.0.5 (PubChem Release 2019.06.18)*

▷ PubChem

408 ⟋ 2.1.3 InChI Key

HUMNYLRZRPPJDN-UHFFFAOYSA-N
*Computed by InChI 1.0.5 (PubChem Release 2019.06.18)*

▷ PubChem

410 ⟋ 2.1.4 Canonical SMILES

C1=CC=C(C=C1)C=O
*Computed by OEChem 2.1.5 (PubChem Release 2019.06.18)*

▷ PubChem

*FIG. 4*

Clustering of SMILES embeddings using t-SNE

LEGEND
Fluoro 902
Cyclo 904
Imine 906
Bromo 908
Chloro 910
Nitro 912
Phosphate 914
Sulfonamide 916

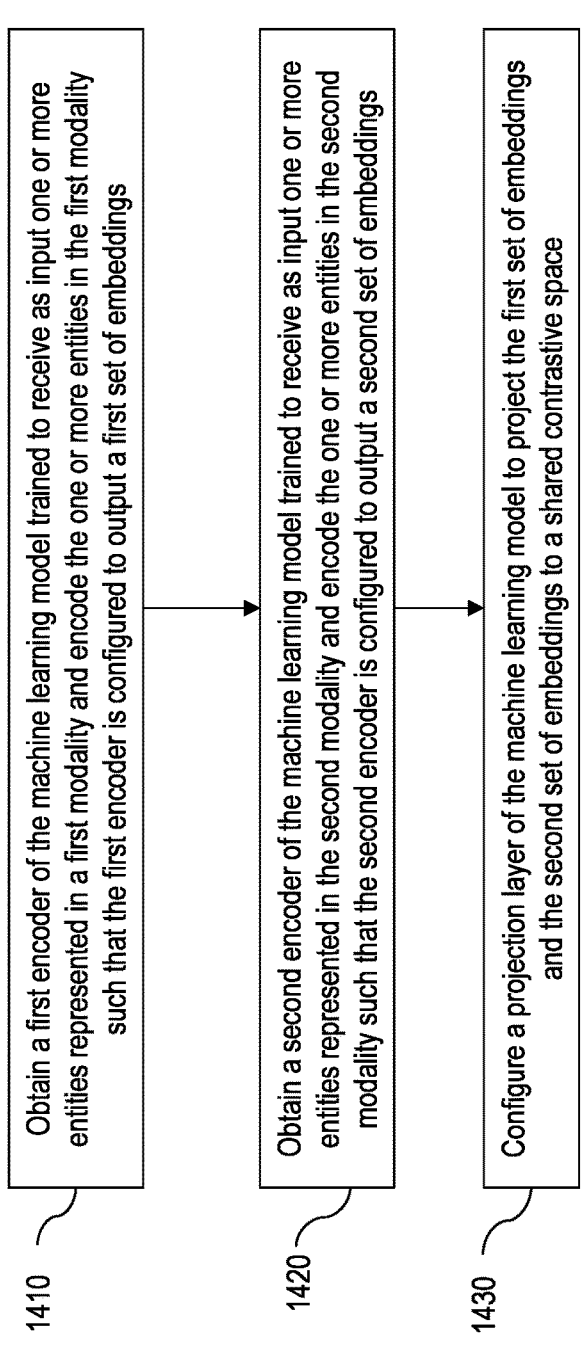

1410   Obtain a first encoder of the machine learning model trained to receive as input one or more entities represented in a first modality and encode the one or more entities in the first modality such that the first encoder is configured to output a first set of embeddings 1420   Obtain a second encoder of the machine learning model trained to receive as input one or more entities represented in the second modality and encode the one or more entities in the second modality such that the second encoder is configured to output a second set of embeddings 1430   Configure a projection layer of the machine learning model to project the first set of embeddings and the second set of embeddings to a shared contrastive space

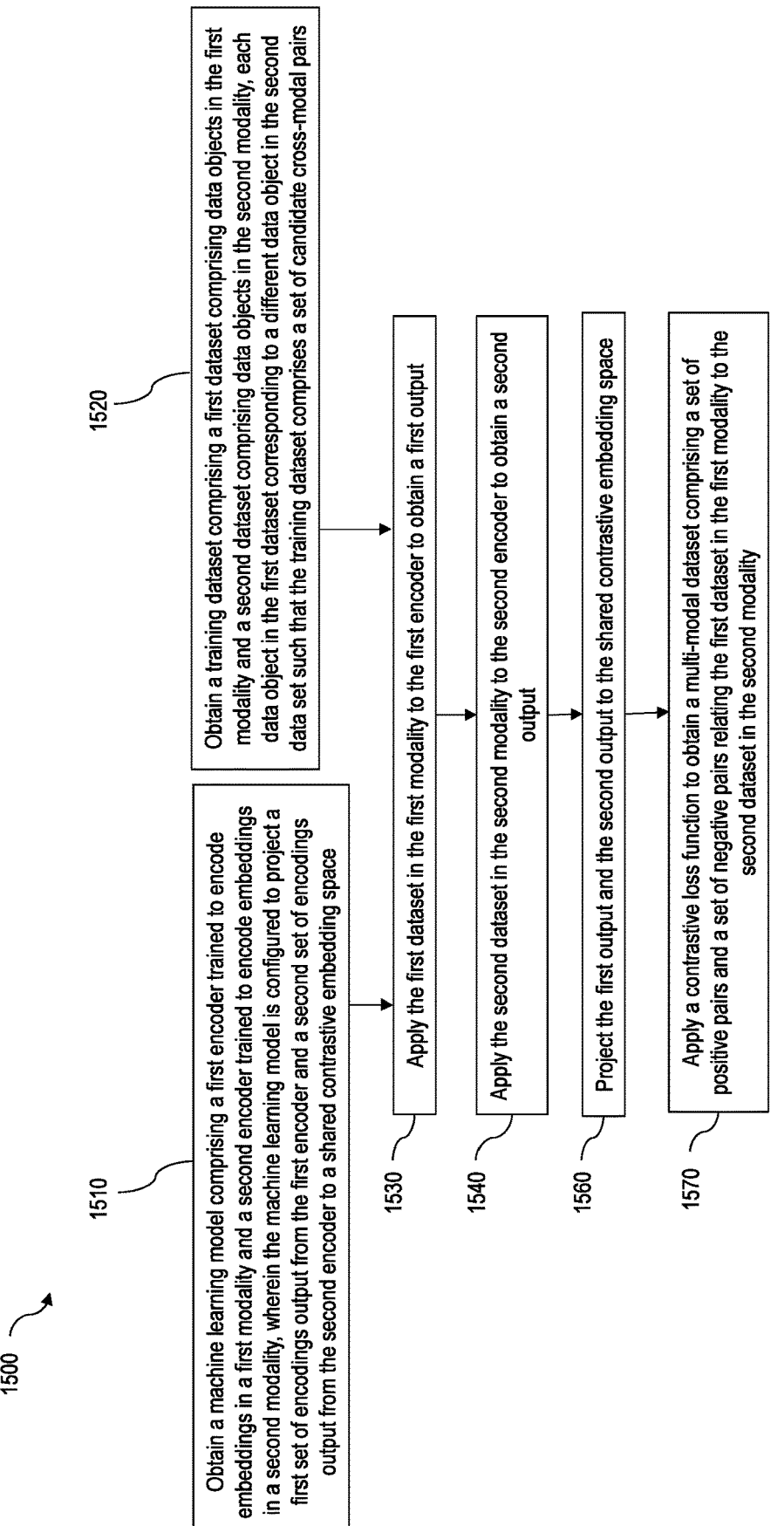

1500

1510

Obtain a machine learning model comprising a first encoder trained to encode embeddings in a first modality and a second encoder trained to encode embeddings in a second modality, wherein the machine learning model is configured to project a first set of encodings output from the first encoder and a second set of encodings output from the second encoder to a shared contrastive embedding space

1520

Obtain a training dataset comprising a first dataset comprising data objects in the first modality and a second dataset comprising data objects in the second modality, each data object in the first dataset corresponding to a different data object in the second data set such that the training dataset comprises a set of candidate cross-modal pairs

1530

Apply the first dataset in the first modality to the first encoder to obtain a first output

1540

Apply the second dataset in the second modality to the second encoder to obtain a second output

1560

Project the first output and the second output to the shared contrastive embedding space

1570

Apply a contrastive loss function to obtain a multi-modal dataset comprising a set of positive pairs and a set of negative pairs relating the first dataset in the first modality to the second dataset in the second modality

FIG. 15

MULTIMODAL DOMAIN EMBEDDINGS VIA CONTRASTIVE LEARNING

BACKGROUND

Quantitative representation of molecules is very useful for computer-aided chemical discoveries, particularly where molecules are embedded as numerical vectors in the high-dimensional chemical space in support of molecular grouping, differentiating, and designing.

A core concept to determine the effectiveness of a molecular embedding approach is called molecular similarity, or the idea that molecules sharing similar structural properties tend to have shorter physical distances in the embedding space while molecules that have dissimilar properties can be separated apart and indicated by low similarity scores. Molecular similarity is fundamental in drug discoveries, with the observation that similar structure fragments of different molecules lead to similar biological activities. With encoded structural and functional properties, molecular embeddings also help in molecular property prediction tasks related to molecular solubility, toxicity, transport inhibition and so on, as well as interaction tasks across different molecules. In practice, pharmaceutical industries are empowered by molecular virtual screening for compound filtering and selection on millions of compounds, in place of extensive lab experimentation. However, molecular representation generation is a difficult task and there are several limitations to existing approaches.

Conventional methods used for performing molecular embedding and fingerprint generation rely heavily on molecular fragment-level operations. A representative of such methods is a Morgan fingerprint, as known as Extended-Connectivity Fingerprint (ECFP), where a fixed binary hash function is applied on each atom and its neighbor path. Because these kinds of methods focus on local features only, these conventional systems are only able to compare similarities between local regions and not between molecules at a global level (i.e., analyzing the molecule as whole entity). Notably, without a global analysis of the molecules, functional activity similarities and even structural similarities are hidden to the analysis systems. This can degrade the overall quality and accuracy of the results returned when the systems receive queries against the molecular data. Additionally, these conventional techniques can limit and degrade the quality of downstream tasks and applications, such as searching for drugs similar to a target drug and predicting drug-to-drug interactions when systems are using only the fragmented molecular embedding data.

Since the emergence of deep learning, just like the revolution in many other research areas, such as image perception, speech recognition, and natural language processing, deep learning has also achieved success in cheminformatics and drug discoveries on a variety of tasks such as adverse drug reaction prediction, binding affinity prediction and molecular representation generation. By way of example, advances in natural language processing, like long-short-term memory (LSTM), enable encoding of textual representations in the chemical domain. However, these existing methods and systems have focused on unimodal embedding generation and analysis. Because of this, these deep learning models are limited to returning results from only the same modality as the initial query is received in. Additionally, in some datasets where molecule entities are only represented by some but not all modalities, the models are unable to detect similar molecules unless they are labeled or represented in the primary modality that the model is trained on.

Furthermore, such models often require an encoder and decoder architecture, where inputs are initially encoded. However, to perform embedding analysis and retrieve similar entities represented in the same modality, the embeddings must be reconstructed using a decoder. This increases the storage needed for the model layers and input/output data caching, as well as increases the computational expense of processing the embedding data.

The foregoing traditional models, particularly when applied to molecular similarity tasks, experience a significant waste of computational expense during processing for at least the reasons mentioned above, including requiring a decoder in the model architecture and performing an additional reconstruction step. Furthermore, the models are not applicable to global level molecular analysis because they are limited to a fragment analysis. Finally, the models are limited to analyzing embeddings in the same domain and in the same modality. Thus, they are not scalable to the large datasets available, such as those in the chemical domain, where multiple modalities are used to represent the same molecule.

Accordingly, there is an on-going need and desire for improved systems, methods, and devices for molecular embedding generation, and particularly, for improved systems, methods, and devices that can be utilized to improve molecular similarity analysis at a global level, so as to more efficiently and effectively perform molecular similarity, drug similarity and drug interaction prediction.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments disclosed herein relate to systems, methods, and devices that are configured to facilitate multimodal in-domain embedding analysis.

Disclosed systems are configured to build a machine learning model that is trainable to perform in-domain embedding analysis. For example, the disclosed systems build the machine learning model by obtaining a first encoder that is trained to receive input from one or more entities represented in a first modality and to encode the one or more entities in the first modality such that the first encoder is configured to output a first set of embeddings, as well as a second encoder that is trained to receive as input one or more entities represented in the second modality and to encode the one or more entities in the second modality, such that the second encoder is configured to output a second set of embeddings. The disclosed systems also build the machine learning model with a projection layer that is configured to project the first set of embeddings and the second set of embeddings to a shared contrastive space.

Disclosed systems are also directed to systems and methods for training a machine learning model, such as the foregoing machine learning model having a first encoder trained to encode embeddings in a first modality and a second encoder trained to encode embeddings in a second modality, to perform multi-modal embedding generation and analysis. In such configurations, the disclosed systems obtain the machine learning model and project a first set of encodings output from the first encoder and a second set of encodings output from the second encoder to a shared contrastive embedding space.

Disclosed systems are also configured to obtain a composite training data set that is composed of first dataset comprising data objects in the first modality and a second dataset comprising data objects in the second modality, wherein each data object in the first dataset corresponds to a different data object in the second data set, and such that the composite training dataset comprises a set of candidate cross-modal pairs.

Disclosed systems are also configured, subsequently to obtaining the composite training dataset, to apply the first dataset in the first modality to the first encoder to obtain a first output, apply the second dataset in the second modality to the second encoder to obtain a second output, project the first output and the second output to the shared contrastive embedding space, and apply a contrastive loss function to obtain a multi-modal dataset comprising a set of positive pairs and a set of negative pairs relating the first dataset in the first modality to the second dataset in the second modality.

Disclosed embodiments further include, but are not limited to, specific use scenarios such as methods for performing molecularity similarity and drug prediction analysis. For example, some disclosed embodiments are directed to specific use scenarios for obtaining a machine learning model comprising a first encoder configured to encode embeddings in a first molecular modality and a second encoder configured to encode embeddings in a second molecular modality, wherein the machine learning model is configured to project a first set of encodings output from the first encoder and a second set of encodings output from the second encoder to a multimodal molecular embedding space.

Some disclosed systems obtain a training dataset comprising a first dataset comprising molecular representations in the first modality and a second dataset comprising molecular representations in the second modality. In such scenarios, each molecular representation in the first dataset (i) are associated with a particular molecule and (ii) corresponds to at least one molecular representation in the second dataset that is associated with the particular molecule, such that the training dataset comprises a set of candidate cross-modal molecular pairs.

Disclosed embodiments also include systems and methods for training machine learning models with the training datasets to configure the machine learning models to perform molecular similarity analysis.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 3 illustrates an example embodiment for a process flow diagram for using a machine learning model to generate multi-modal contrastive embeddings.

FIG. 4 illustrates an example embodiment of different representations or modalities used to represent molecules.

FIG. 14 illustrates a process flow diagram comprising a plurality of acts associated with a method for building a machine learning model configured to generate multimodal contrastive embeddings.

FIG. 15 illustrates a process flow diagram comprising a plurality of acts associated with a method for training a machine learning model configured to generate multimodal contrastive embeddings.

DETAILED DESCRIPTION

Figure 1:
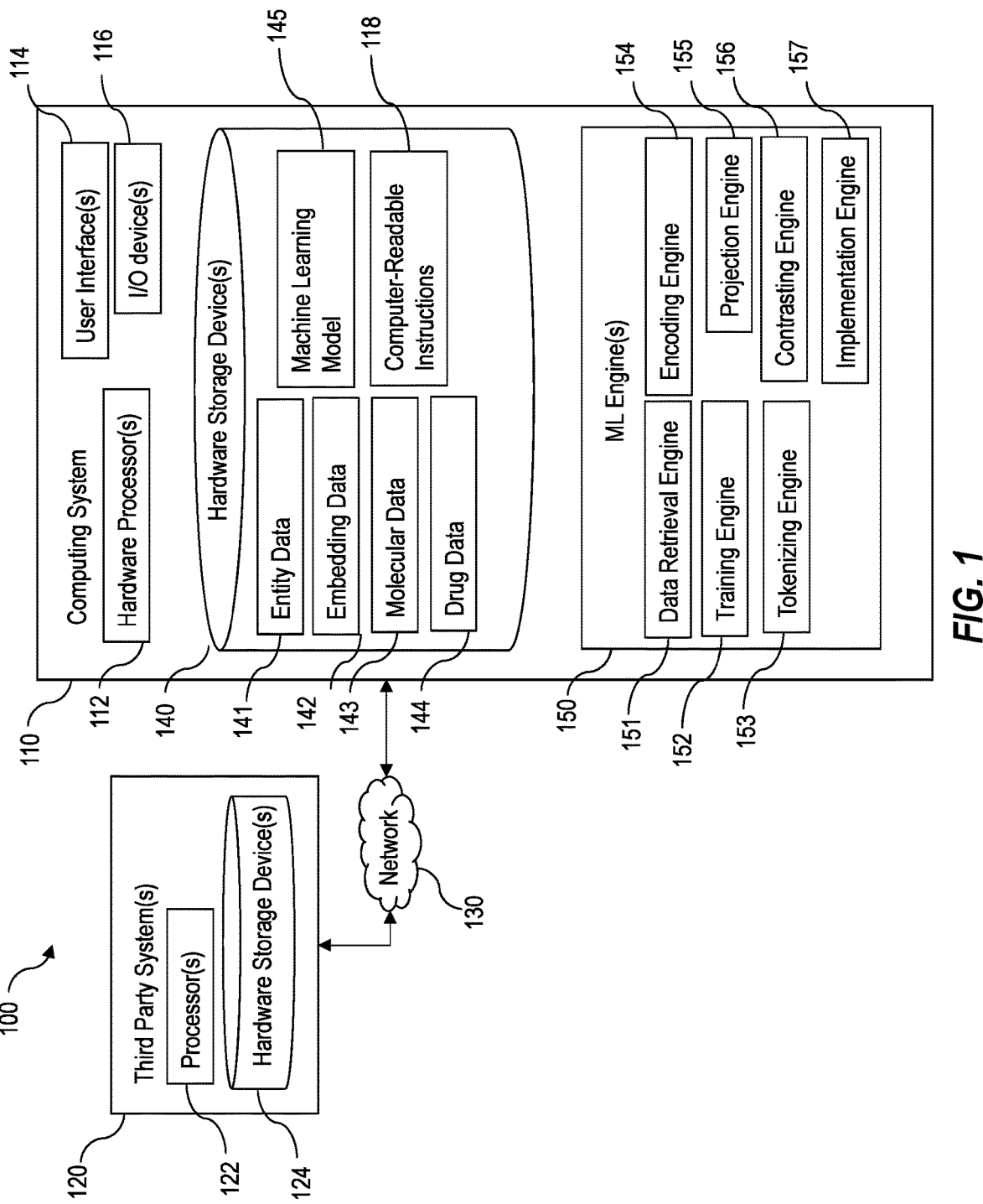
FIG. 1 illustrates an example architecture that includes a computing system that includes and/or that is capable of being utilized to implement the disclosed embodiments.

Embodiments disclosed herein relate to systems, methods, and devices that are configured to facilitate in-domain embedding generation and analysis, and even more particularly, for systems, methods, and devices that can be utilized to generate embeddings across multiple modalities. Disclosed embodiments are operable to in-domain embedding analysis by generating and training a machine learning model configured to generate multimodal contrastive embeddings.

The disclosed embodiments provide many technical advantages over existing systems, methods, and devices. Molecular embedding encodes each molecular as a property-preserving vector, and thus provides an interpretative way for molecular clustering and similarity comparison. Joint learning with a self-supervised contrastive loss for multi-modal representation beneficially provides rich information for molecular searches, drug searches, and drug interaction predictions. As a result, the multi-modal embedding space is not only able to identify molecules that are similar in structures but is also sensitive to functional groups. Thus, the self-supervised contrastive learning framework beneficially provides an embedding space for in-domain exploration between different modalities. In particular, the embedding space is configurable for chemical domain exploration and drug discoveries.

Inspired by the recent success of contrastive learning in multimodal vision and language research, disclosed embodiments are directed to systems and methods referred to as MM-Deacon (multimodal molecular domain embedding analysis via contrastive learning) for multimodal molecular embedding generation. MM-Deacon uses Transformers as base encoders and projects embeddings from encoders to a common space across different modalities. After projection, contrastive learning is enforced to push close the embeddings of positive cross-modal pairs and push away the embeddings of negative pairs.

In some embodiments, SMILES and IUPAC are selected as the interested modalities in the molecular domain, wherein SMILES is an abbreviation for simplified molecular-input line-entry system, a widely known and used database to represent molecular structures ASCII strings, while IUPAC (the International Union of Pure and Applied Chemistry) provides nomenclature that provides global standards for names, symbols and units for organizing molecular structures by spoken words.

As described herein, and rather than using SMILES and IUPAC for seq2seq translation applications at the fragment level, the disclosed embodiments are directed to obtaining positive and negative SMILES-IUPAC pairs and contrasting their embeddings in global molecule level, instead of fragment level, with cosine similarity. As further described throughout this disclosure, the disclosed embodiments can be utilized to facilitate the application/integration of different descriptors of molecules to a common embedding space and such that the disclosed embeddings can leverage and sometimes maximize corresponding information of multiple different domains such as, but not limited to, the SMILES and IUPAC modalities.

Some disclosed embodiments are directed to utilizing SMILES-IUPAC matching information for molecular embedding space generation in a contrastive learning framework. Beneficially, such molecular embeddings are not generated in an encoder-decoder setting which requires a reconstruction of embeddings for analysis. For example, in some architectures, a decoder is needed to reconstruct a molecule back to itself in order to supervise learning in the embedding space. The disclosed embodiments more efficiently provide embedding space that does not require a decoder or subsequent reconstruction. Furthermore, the disclosed embodiments facilitate embedding generation and analysis in both a unimodal and multimodal navigation across the embedding space. Additionally, since the model is trained in a self-supervised manner, the model is not limited to labeled data, and thus, has the ability to leverage large-scaled unlabeled data sets.

Attention will now be first directed to FIG. 1, which illustrates a computing system 110 that may include or be used to implement aspects of the claimed invention. In particular, the computing system 110 is configured, as described throughout this disclosure, to generate, train, and operate a multi-modal analysis model configured to generate in-domain multi-modal embeddings and facilitate embedding analysis via contrastive learning.

The computing system 110 is currently illustrated as part of a computing environment 100 that also includes third-party system(s) 120 (which can also be configured as remote systems) in communication (via a network 130) with computing system 110. These remote systems may include distributed portions of the computing system 110. Alternatively, or additionally, the third-party system(s) 120 include the third-party knowledge base(s) 126 that are referenced herein.

The computing system 110 is also illustrated as including one or more processor(s) (such as one or more hardware processor(s)) 112 and a storage (i.e., hardware storage device(s) 140) storing computer-readable instructions 118 wherein one or more of the hardware storage device(s) 140 is able to house any number of data types and any number of computer-readable instructions 118 by which the computing system 110 is configured to implement one or more aspects of the disclosed embodiments when the computer-readable instructions 118 are executed by the one or more processor(s) 112. The computing system 110 is also shown including user interface(s) 114 and input/output (I/O) device(s) 116.

Hardware storage device(s) 140 is currently shown as a single storage unit. However, it will be appreciated that the hardware storage device(s) 140 is/are also sometimes implemented as a distributed storage which is distributed throughout several separate and sometimes remote systems and/or third-party system(s) 120. In this regard, it will be appreciated that the computing system 110 can comprise a distributed system with one or more of the components of computing system 110 being maintained/run by different discrete systems that are remote from each other and that each perform different tasks. In some instances, for example, the computing system 110 operates as a plurality of distributed systems that perform similar and/or shared tasks for implementing the disclosed functionality, such as in a distributed cloud environment.

The hardware storage device(s) 140 are configured to store the different data types including entity data 141, embedding data 142, molecular data 143, and drug data 144, described herein. Entity data 141 refers to data about particular entities that are of interest. The entities are typically related to a particular domain. For example, in the chemical domain, the entities are configured as molecules and/or molecular sequences. In an enterprise domain, the entities may refer to users of the enterprise system. It should be appreciated that the systems and methods described herein are described as applied to the chemical domain as an example; however, the systems and methods are adaptable to any number of domains, wherein different modalities are inter-domain or intra-domain.

Each entity included in the entity data 141 is referenced or represented by one or more modalities. For example, a "dog" entity is represented by a particular photograph in an image modality and the word "dog" in a text modality. "Dog" could also be represented by an audio clip including a recording of a dog barking, wherein "dog" is then represented by an audio modality. Each of these representations is related because they represent the same or equivalent entity. Each representation in the respective modality is processed to generate an embedding for each representation. These embeddings are included in the embedding data 142 which is able to be projected to a shared multi-modal embedding space. Once projected to the shared multi-modal embedding space, various functions, including contrastive loss functions, are applicable to extract relational information about the different embeddings, and thus their corresponding entities.

In the chemical domain, the entity data 141 is configured as molecular data 143 and/or drug data 144. In molecular data 143, the entities are molecules or specific molecular sequences. The molecular data 143 also includes structural information about each molecule, as well as known biological/chemical activity. In drug data 144, the entities are drugs, including drug names, FDA-approval status, date of FDA-approval, structural information, functional activity information, and drug-drug interaction information.

The storage (e.g., hardware storage device(s) 140) also stores or includes computer-readable instructions 118 that are executable by the systems hardware processors for instantiating or implementing the disclosed models and/or engines shown in computing system 110 (e.g., the machine learning model 145.

The computing system 110 is configured to build a machine learning model 145 that is trainable to perform in-domain embedding analysis. One or more computer-readable instructions that are executable by the one or more processors to configure the computing system to obtain a first encoder of the machine learning model trained to receive as input one or more entities represented in a first modality and encode the one or more entities in the first modality such that the first encoder is configured to output a first set of embeddings. The computing system 110 is also configured to obtain a second encoder of the machine learning model trained to receive as input one or more entities represented in the second modality and encode the one or more entities in the second modality such that the second encoder is configured to output a second set of embeddings, wherein computing system 110 configures a projection layer of the machine learning model to project the first set of embeddings and the second set of embeddings to a shared contrastive space.

Additionally, the machine learning model 145 comprises a global average pooling layer that is configured to each set of embeddings prior to the projection layer projecting the first set of embeddings and second set of embeddings to the shared contrastive space.

The referenced models are configured as machine learning models or machine learned models, such as deep learning models and/or algorithms and/or neural networks. In some instances, the one or more models are configured as engines or processing systems (e.g., computing systems integrated within computing system 110), wherein each engine (i.e., model) comprises its own discrete set of one or more processors (e.g., hardware processor(s) 112) and computer-readable instructions 118.

An additional storage unit for storing machine learning (ML) Engine(s) 150 is presently shown in FIG. 1 as storing a plurality of machine learning models and/or engines. For example, computing system 110 comprises one or more of the following: a data retrieval engine 151, a training engine 152, a tokenizing engine 153, an encoding engine 154, a projection engine 155, a contrasting engine 156, and an implementation engine 157, which are individually and/or collectively configured to implement the different functionality described herein.

For example, the data retrieval engine 151 is configured to locate and access data sources, databases, and/or storage devices comprising one or more data types from which the data retrieval engine 151 can extract sets or subsets of data to be used as training data or entity data (e.g., new text data/document data/molecular data). The data retrieval engine 151 receives data (e.g., molecular data 143 and/or drug data 144) from the databases and/or hardware storage devices, wherein the data retrieval engine 151 is configured to reformat or otherwise augment the received data to be used as training data. Additionally, or alternatively, the data retrieval engine 151 is in communication with one or more remote systems (e.g., third-party system(s) 120) comprising third-party datasets and/or data sources.

The data retrieval engine 151 accesses electronic content comprising various kinds of molecular representations such as textual sequences, ground truth relations among sequences, unlabeled molecular meta information, and/or graphics of molecules. The data retrieval engine 151 is configured to retrieve and generate training datasets comprising data for a target relation. In some instances, if desired format (e.g., textual sequence in a specific format) of the data is not available, the data retrieval engine 151 is able to convert available format to desired format with third party systems 120. The data retrieval engine 151 is a smart engine that is able to learn optimal dataset extraction processes to provide a sufficient amount of data in a timely manner as well as retrieve data that is most applicable to the desired applications for which the machine learning models/engines will be trained. For example, the data retrieval engine 151 can learn which databases and/or datasets will generate training data that will train a model (e.g., for a specific query or specific task) to increase accuracy, efficiency, and efficacy of that model in the desired natural language processing techniques.

The data retrieval engine 151 locates, selects, and/or stores raw recorded source data such that the data retrieval engine 151 is in communication with one or more other ML engine(s) and/or models included in computing system 110. In such instances, the other engines in communication with the data retrieval engine 151 are able to receive data that has been retrieved (i.e., extracted, pulled, etc.) from one or more data sources such that the received data is further augmented and/or applied to downstream processes. For example, the data retrieval engine 151 is in communication with the training engine 152 and/or implementation engine 157.

The training engine 152 is in communication with one or more of the data retrieval engine 151 and/or the implementation engine 157. In such embodiments, the training engine 152 is configured to receive one or more sets of training data (e.g., cross-modal pairs or tuples extracted from entity data 141 and/or embedding data 142) from the data retrieval engine 151. After receiving training data relevant to a particular application or task (e.g., a target relation), the training engine 152 trains one or more models on the training data. The training engine 152 is configured to train a model via unsupervised training, such as self-supervision, or distant supervision, and/or supervised training (i.e., direct supervision). The training engine 152 is figured to train the machine learning model 145 on training data to generate multi-modal embeddings.

The training engine 152 is configured to train a first tokenizer of the machine learning model to tokenize the one or more entities in the first modality into a first set of tokens prior to the first encoder receiving as input the one or more entities in the first modality; and train a second tokenizer of the machine learning model to tokenize the one or more entities in the second modality into a second set of tokens prior to the second encoder receiving as input the one or more entities in the second modality. The first encoder and second encoder being configured to receive the first and second sets of tokens at a global level.

The training engine 152 is also configured for training the machine learning model with the training dataset to configure the machine learning model to perform molecular similarity analysis by at least: applying the first dataset in the first modality to the first encoder to obtain a first set of molecular embeddings, applying the second dataset in the second modality to the second encoder to obtain a second set of molecular embeddings, projecting the first set of molecular embeddings and the second set of molecular embeddings to the multimodal molecular embedding space, and applying a contrastive loss function to obtain a multimodal dataset comprising a set of positive pairs and a set of negative pairs relating the first dataset in the first modality to the second dataset in the second modality, such that the machine learning model is trained to predict molecular similarity based on learning the set of positive pairs and set of negative pairs.

The computing system 110 also includes an implementation engine 157 in communication with any one of the models and/or ML engine(s) 150 (or all of the models/ engines) included in the computing system 110 such that the implementation engine 157 is configured to implement, initiate, or run one or more functions of the plurality of ML engine(s) 150. In one example, the implementation engine 157 is configured to operate the data retrieval engines 151 so that the data retrieval engine 151 retrieves data at the appropriate time to be able to generate training data for the training engine 152. The implementation engine 157 facilitates the process communication and timing of communication between one or more of the ML engine(s) 150 and is configured to implement and operate a machine learning model (or one or more of the ML engine(s) 150).

In some embodiments, the implementation engine 157 is configured as a query engine that is configured to receive a query, such as a molecular query or a drug query and return results that are predicted to be similar to a target entity identified in the query.

The implementation engine 157 is configured to obtain a machine learning model comprising a first encoder trained to encode embeddings in a first modality and a second encoder trained to encode embeddings in a second modality, wherein the machine learning model is configured to project a first set of encodings output from the first encoder and a second set of encodings output from the second encoder to a shared contrastive embedding space. The implementation engine 157 also causes the system to obtain a training dataset comprising a first dataset comprising data objects in the first modality and a second dataset comprising data objects in the second modality. Each data object in the first dataset corresponds to a different data object in the second data set such that the training dataset comprises a set of candidate cross-modal pairs.

Subsequently, the implementation engine 157 is configured to apply the first dataset in the first modality to the first encoder to obtain a first output, apply the second dataset in the second modality to the second encoder to obtain a second output, project the first output and the second output to the shared contrastive embedding space, and apply a contrastive loss function to obtain a multi-modal dataset comprising a set of positive pairs and a set of negative pairs relating the first dataset in the first modality to the second dataset in the second modality.

The implementation engine 157 is also configured to apply a target entity in the first modality as query to the machine learning model 145 to obtain a third output in the first modality (i.e., unimodal embedding generation). The third output of the target entity is then applicable as a query to obtain entities predicted to be similar to the target entity. In some instances, the third output of the target entity comprises a cluster map depicting a plurality of unimodal or multi-modal embeddings having been projected to a shared embedding space.

Based on information obtained for a particular modality, hidden links are identified among clusters included in the cluster map. The hidden links refer to knowledge discovery. For example, different clusters are regarded as different groupings of entities in the embedding space. For entities in the same cluster, the entities share similar properties. Thus, by taking a cluster as a query, the system is able to find other clusters that have similar properties to the query cluster. For example, the calculation is based on intra-cluster statistical properties of entities. Additionally, the system is able to locate clusters nearby the query. The calculations are then based on the coordinates of each cluster's centroid. The system is also able to compare relations of pairs of clusters.

If one cluster (or its centroid) of a cluster map is designated as a graph node, the relations of the cluster to other clusters are denoted as graph edges or links, such as those found in graph theory. The knowledge revealed by the relations of the certain clusters can be used to discover new knowledge (i.e., hidden links). Links refers to the relationship between different clusters based on cluster-level properties.

The computing system is in communication with third-party system(s) 120 comprising one or more processor(s) 122, one or more of the computer-readable instructions 118, and one or more hardware storage device(s) 124. It is anticipated that, in some instances, the third-party system(s) 120 further comprise databases housing data that could be used as training data, for example, newly discovered molecules not included in local storage. Additionally, or alternatively, the third-party system(s) 120 include machine learning systems external to the computing system 110. The third-party system(s) 120 are software programs or application.

Figure 2:
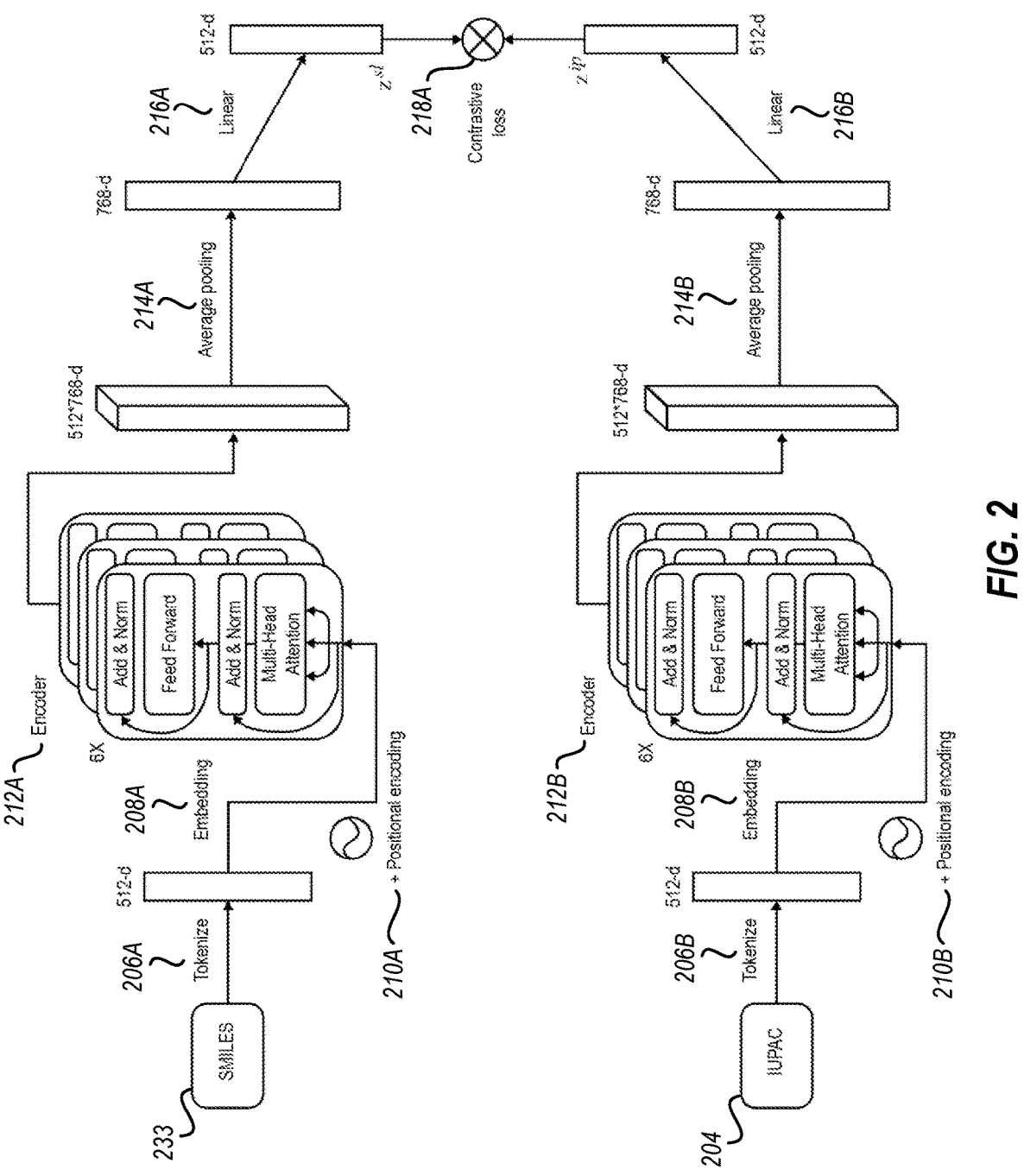
FIG. 2 illustrates an example embodiment for a process flow diagram for generating multi-modal contrastive embeddings.

Attention will now be directed to FIG. 2, which illustrates an example embodiment for a process flow diagram for using a machine learning model to generate multi-modal contrastive embeddings. The model is configured to take in different modalities at separate branches. Where the modality is a text-based modality (e.g., SMILES 202 and/or IUPAC 204), at the beginning of each branch, the input text string is tokenized (e.g., tokenize 206A and tokenize 206B) and embedded into a numeric matrix representation (e.g., embedding 208A and embedding 208B). The order of the token list is preserved by a positional encoding (e.g., positional encoding 210A and positional encoding 210B). The numeric matrix representation and positional embedding are ingested by an encoder 212A and 212B. In some instances, the encoder is configured as a plurality of transformer encoder blocks (e.g., the encoder comprises six Transformer encoder blocks).

A Transformer encoder block has a plurality of sublayers (e.g., two sublayers), a multi-head attention layer, and a fully connected feed-forward layer. Each sub-layer is followed by a residual connection and a layer normalization. The multi-head attention layer takes all positions into consideration and in this way acquires long-dependency information. Afterwards, a global average pooling layer (e.g., average pooling 214A and average pooling 214B) is used to integrate features at all positions. A linear layer (e.g., linear 216A and linear 216B) is used to project the integrated feature vector to the contrastive space via contrastive loss function (e.g., embedding space 218). Thus, the final embeddings of the numerical matrix representation is expressed as the following equation: z=Linear (AvgPool (fEn (x+px))).

The maximum length of the input token vector size is pre-definable and adjustable. For example, in some instances, the maximum length of the input token vector size is set as 512. In such instances, the number of self-attention heads is twelve and a hidden size of 768 for each Transformer encoder block. The final linear layer projects the vector from length of 768 to 512 (e.g., the hidden size is projected to the maximum length size).

The objective is to align pairs of modalities by maximizing mutual information of positive pairs and discriminating negative pairs in the embedding space. The negative pairs are not constructed manually. Instead, the negative pairs are obtained in minibatches during training. Considering that in a minibatch of N number of dual modality pairs as input, in the correlation matrix of N first modalities and N second modalities, N positive pairs and $N^2-N$ negative pairs are formed. For the i-th first modality, the only positive pair mate is the i-th second modality, while the rest N−1 second modalities are all negative in relation to the i-th first modality.

An optimizer (e.g., AdamW) with a particular learning rate (e.g., $10^-6$) is used, wherein the model is trained on a particular GPU configuration (e.g., 120 V100 GPUs). A batch size is determined (e.g., 16) which is the set as the maximum possible batch size that can fit on each GPU. Early stop is adopted, which results in training of a plurality of epochs.

Attention will now be directed to FIG. 3, which illustrates an example embodiment for a process flow diagram for generating multi-modal contrastive embeddings. While the model in FIG. 2 is shown to intake a plurality of text-based modalities, it should be appreciated that the model is trainable to receive as input other types of modalities. For example, as illustrated in FIG. 3, a first modality is a text-based modality and a second modality is an image-based modality. In such configurations, a plurality of image samples 302A and a plurality of textual samples 302B are processed in a similar manner as described in reference to FIG. 2, including having a text encoder 304B which encodes the string and facilitates the projection of the entity in the first modality to the shared contrastive space 306.

The plurality of image samples 302A is encoded with an image encoder 304A, wherein the embeddings of both the image samples and the textual samples are projected to the same shared multi-modal contrastive space 306. Positive pairs are found along the diagonal, while negative pairs are simultaneously generated in the rest of the embedding space. This constitutes the contrastive training between pairs of molecular modalities.

Subsequently, a dataset is created that is a dataset classifier from the labeled text, wherein the embedding space is queried to perform zero-shot prediction (e.g., image to text retrieval). For example, the system is queried with an image of a particular molecule (e.g., image 310), wherein the system returns the text string 312 with the corresponding textual candidate 312 which corresponds to the image of particular molecule and is ranked the best-matched text from the possible textual candidates. The system marks the corresponding positive (e.g., as shown in bold typeface) and negative examples (e.g., as shown in regular typeface).

Attention will now be directed to FIG. 4, which illustrates an example embodiment of different representations or modalities used to represent molecules. This is representative of a large-scale dataset that has cross-modal pairs, particular for the chemical domain. For example, PubChem is a large-scale publicly available dataset that hold information for millions of chemical compounds and their activities. Molecules that have both canonical SMILES and preferred IUPAC name in their descriptors are extractable to form a plurality of SMILES-IUPAC pairs.

In some embodiments, mutually exclusive datasets comprising various numbers of pairs are selected to train, validate, and test the model. For example, ten million pairs are selected for the training dataset, 100 k pairs are selected for the validation dataset, and 100 k pairs are selected for the test dataset. As illustrated in FIG. 4, information for the compound Benzaldehyde 402 is shown. There are several different names and identifiers including the IUPAC name 404, the InCHI representation 406, the InChI Key 408, and the canonical SMILES representation 410. Each of the aforementioned names and identifiers is configured as a different modality representing the same entity for Benzaldehyde, within the chemical domain.

Figure 5:
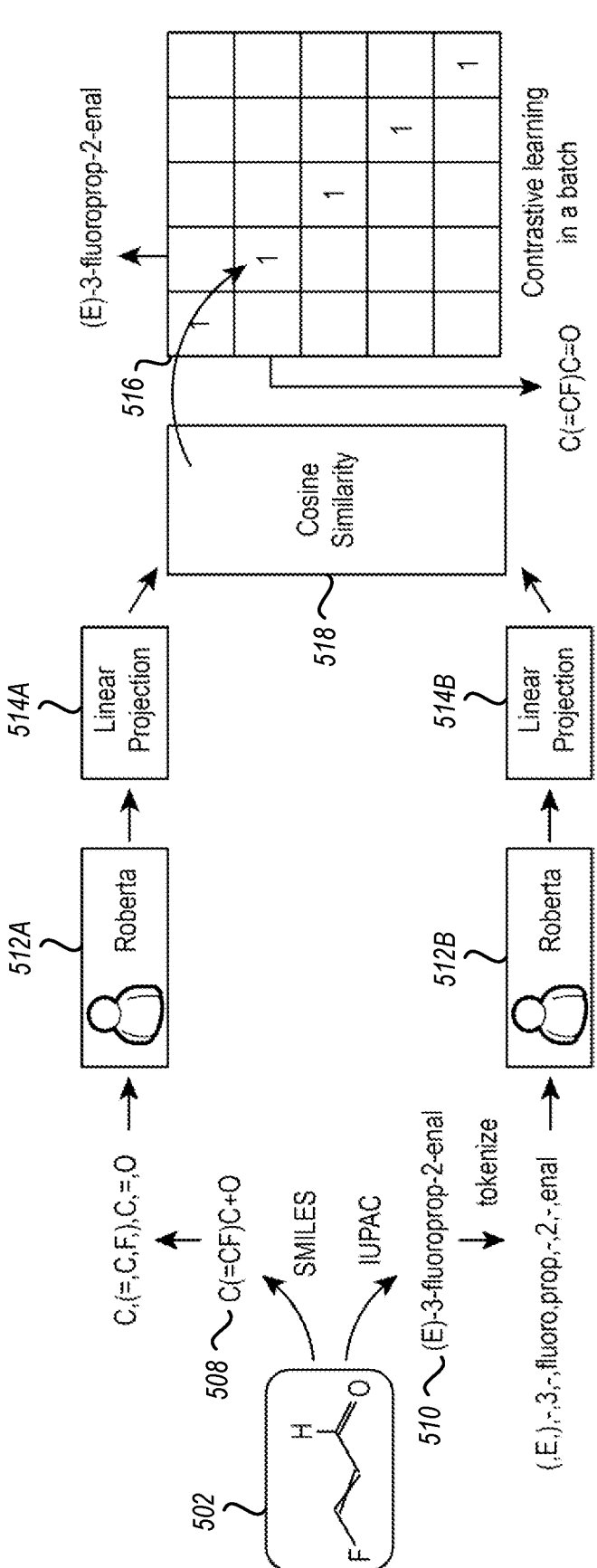
FIG. 5 illustrates an example embodiment for a process flow diagram for using a machine learning model to generate multimodal molecular embeddings in a contrastive learning space.

Attention will now be directed to FIG. 5, which illustrates an example embodiment for a process flow diagram for using a machine learning model to generate multimodal molecular embeddings in a contrastive learning space. For example, FIG. 5 illustrates an example embodiment of generating multimodal molecular embeddings for a particular molecule 502. The molecule 502 is associated with at least two different modalities (e.g., SMILES 504 and IUPAC 506), wherein the model takes SMILES and IUPAC strings as input. The strings (e.g., SMILES string 508 and IUPAC string 510) are first split into lists of tokens by dedicated tokenizers.

For example, in the SMILES modality, C(=CF)C+O is tokenized into C,(=,C,F,),C=,O, and in the IUPAC modality, E-3-fluoroprop-2-enal is tokenized into (,E,)-,3,flouro, prop,-,2,3,-,enal (with commas separating individual tokens). Afterwards, SMILES and IUPAC token vectors as complete respective sets (e.g., tokens at a global level) are encoded individually by separate Transformers (e.g., Roberta 512A, Roberta 512B. Both modalities are then projected to a multimodal molecular embedding space 516 via a linear projection 514A and linear projection 514B, where contrastive loss is enforced to maximize shared features of positive SMILES-IUPAC pairs and discriminate negative SMILES-IUPAC pairs, based on cosine similarity 518.

In some instances, for the SMILES tokenization, a Byte-Pair Encoder is used. In some instances, a regex-based tokenization is used. For IUPACT name tokenization, a rule-based regex tokenizer is used to split IUPAC strings according to their suffixes, prefixes, trivial names, and/or other structural separable information represented by a particular set of characters in the IUPAC string.

Figure 6:
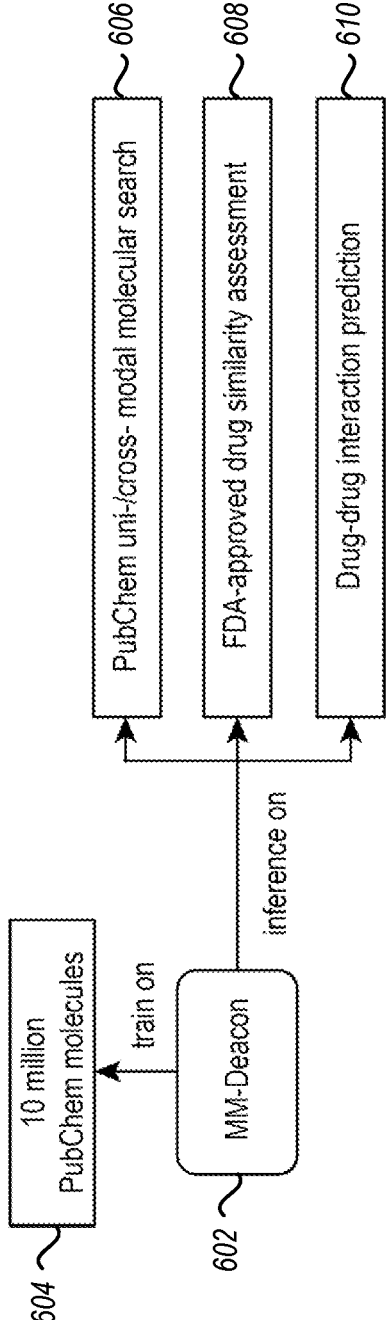
FIG. 6 illustrates an example embodiment of training a machine learning model to perform various tasks, including molecular similarity analysis, drug similarity prediction, and drug interaction prediction.

Attention will now be directed to FIG. 6, which illustrates an example embodiment of training a machine learning model (e.g., MM-Deacon 602) on molecular data (e.g., ten million PubChem molecules 604) to perform various tasks, including molecular similarity analysis (e.g., PubChem uni/cross-modal molecular search 606), drug similarity prediction (e.g., FDA-approved drug similarity assessment 608), and drug interaction prediction (e.g., drug-drug interaction prediction 610). The machine learning model is configured as a deep neural network designed for SMILES-IUPAC joint learning with an object to maximize mutual information across modalities, where SMILES and IUPAC depicting the same molecular are enforced to be represented by the same normalized vector in the embedding space, whereas SMILES and IUAC from different molecules to be represented by orthogonal vectors. Thus, the similarity among molecules can be measured by pair-wise cosine similarity.

Inside the model architecture, Transformers with multi-head self-attention layers (as depicted in FIG. 2) are utilized to encoder SMILES and IUPAC strings. Embeddings from the encoders are pooled globally and projected to the contrastive space. To take full advantage of the capacity of the model, the machine learning model is trained on a large dataset comprising upwards of ten million molecules, for example, from a data source such as PubChem.

To evaluate the quality of the molecular embedding space after training, cross modal search and unimodal search are performed to test on a dataset of a plurality of molecules (e.g., 100 k molecules) which are mutually exclusive from the training dataset. In addition, the machine learning model is configured to perform drug similarity assessments and drug-drug interaction prediction tasks to further demonstrate the quality of the molecular embeddings generated by the model.

There are several different datasets that are usable to train the model. for example, a first training dataset comprises a plurality of molecules (or molecular compounds/or molecular fragments), wherein each molecule is associated with one or more representations or modalities. In some embodiments, the training dataset is representative of the data depicted in FIG. 4. Such a dataset is usable to train the model to perform molecular similarity analysis and generate molecular embeddings. The model is then configured to perform a molecular search in the embedding space given a query vector. For example, given a query vector, similarity scores (e.g., cosine similarity scores) between the query and the search candidates are calculated to determine the ranking. Feature dimension reduction techniques are also used to further investigate the relationships of molecules in a 2D plane.

Additionally, some training datasets comprise a plurality of drugs, for example, selected from an FDA-approved drug list comprising small molecule drugs. In some instances, a target drug is identified/selected, wherein the model is trained or applied to look for relationships between the target drugs and their potent transporter inhibitors to identify alternatives in the embedding space. Such training datasets comprising the plurality of drugs and their corresponding structural information are usable to train the model to perform drug similarity assessments. For the different drugs, the system obtains the molecular embeddings in a particular modality by feeding forward inputs in the modality to the model. Then, based on similarity (e.g., cosine similarity) the drug-drug similarity relationships are mapped.

Some training datasets comprise a drug-drug interaction dataset comprising a plurality of drugs, known interactions between two or more drugs, and non-interactions. In some instances, the drug-drug interaction training dataset (i.e., configured as a drug-drug interaction matrix) is combined with a drug-drug similarity matrix which comprises molecular substructure data extracted from the first training dataset described above. Such training datasets are usable to train the model to predict whether there is an interaction between one drug and another drug. In some instances, the model is able to identify both known interactions and predict previously undetected interactions (i.e., new interactions between drugs). To perform drug-drug interaction prediction, embeddings of pairwise drugs in a first modality are concatenated and a multi-layer perceptron (MLP) network is used to predict the binary labels. The MLP has one or more hidden layers, each with a plurality of neurons (e.g., 200 neurons). Cross-validation is employed to report the results.

Figure 7:
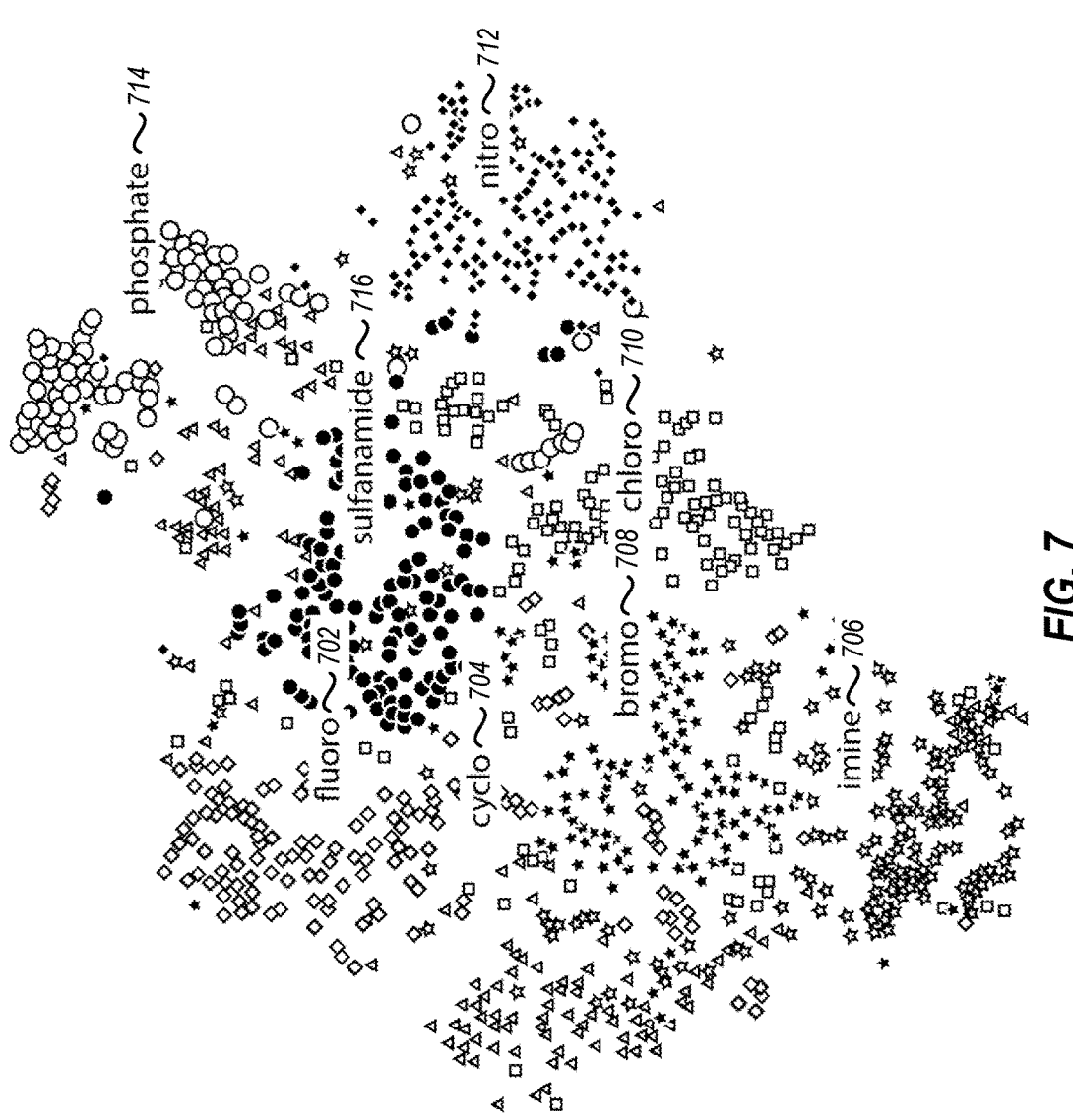
FIG. 7 illustrates an example embodiment of a cluster map for a single modality generated by a machine learning model, for example as depicted in FIG. 5.
Figure 8:
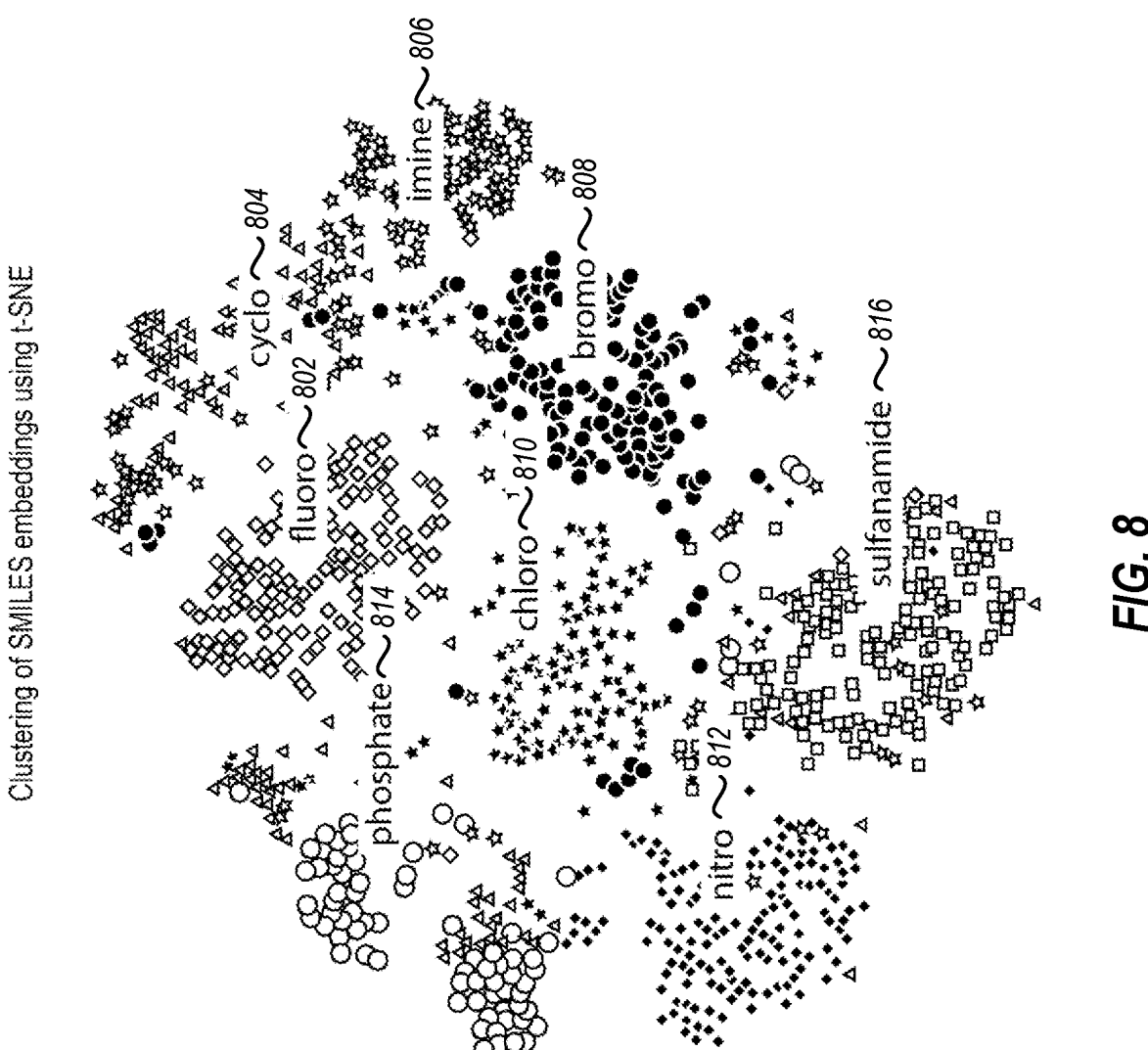
FIG. 8 illustrates an example embodiment of a cluster map for joint modalities generated by a machine learning model, for example as depicted in FIG. 5.

Attention will now be directed to FIGS. 7-8, which depict the sensitivity of the embeddings generated by the model to functional group names or prefixes, which are attributes of the IUPAC nomenclature. A plurality of molecules from different functional groups are extracted (e.g., fluoro 702, cyclo 704, imine 706, bromo 708, chloro 710, nitro 712, phosphate 714, and suflonamide 716). A rule is designated that if the IUPAC names of the molecule includes the name of the functional group and excludes the names of all other groups, then the molecule is labeled as the name of the group. FIG. 7 illustrates an example embodiment of a cluster map for a single modality generated by a machine learning model, for example as depicted in FIG. 5. FIG. 7 displays clustering results based on SMILES embeddings. It should be appreciated that the clustering is presentable in any modality on which the model is trained.

Attention will now be directed to FIG. 8, which illustrates an example embodiment of a cluster map for joint modalities generated by a machine learning model, for example as depicted in FIG. 5. A plurality of molecules from different functional groups are extracted (e.g., fluoro 802, cyclo 804, imine 806, bromo 808, chloro 810, nitro 812, phosphate 814, and suflonamide 816).

The joint embeddings are defined as the dot product of the SMILES embeddings and the IUPAC embeddings after normalization. For clarity, only 200 data points for each group are plotted in the figures. From the clusters in each figure, the molecular embeddings are separable in terms of functional groups, where the joint embeddings have the best separation ability. When compared to the clustering results in FIG. 7, the different joint clustering for each functional group in FIG. 8 is separated more than the different clustering results for each functional group in FIG. 7. Thus, the model beneficially attains a higher quality clustering result with joint embeddings.

The clustering of the different functional groups shows that domain knowledge brought by the different modalities (e.g., IUPAC or SMILES nomenclature) has been encoded in the embedding space, without explicit definition or labeling of the different functional groups. Functional groups are responsible for characteristic chemical reactions of molecules, and thus molecular representation with an awareness of underlying functional groups is beneficial for drug discoveries, which is discussed further in regard to FIGS. 12-13.

Figure 9:
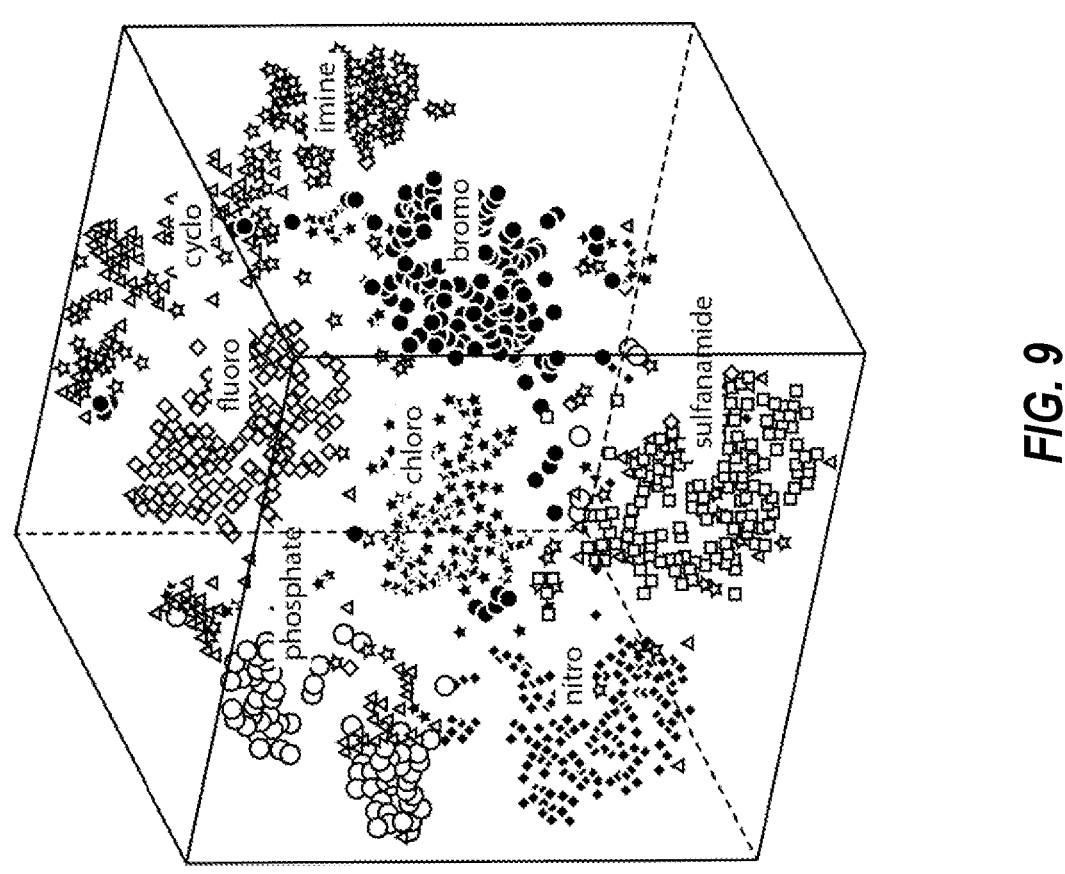
FIG. 9 illustrates an example embodiment of a cluster map for multiple linked modalities generated by a machine learning model, for example as depicted in FIG. 5.

FIG. 9 illustrates an example embodiment of a cluster map for multiple linked modalities generated by a machine learning model, for example as depicted in FIG. 5. In some embodiments, the machine learning model is trained on a plurality of modalities (e.g., at least three modalities), in which clustering results are depicted in a 3D space. A plurality of molecules from different functional groups are extracted (e.g., fluoro 902, cyclo 904, imine 906, bromo 908, chloro 910, nitro 912, phosphate 914, and suflonamide 916).

Attention will now be directed to FIGS. 10A, 10B, 11A, and 11B, which present different molecular search performed by a machine learning described herein. Depending on the search objective, in each figure, either a SMILES or IUPAC strings of the top 5 similar molecules to the query are listed in a right panel, and the corresponding embeddings are projected to a 2D plan in the left panel (e.g., by using UMAP). The top 1,000 molecules are shown being plotted in the left panel. Critical substructures in the queries are present in the top retrieved results.

Figures 10A, 10B:
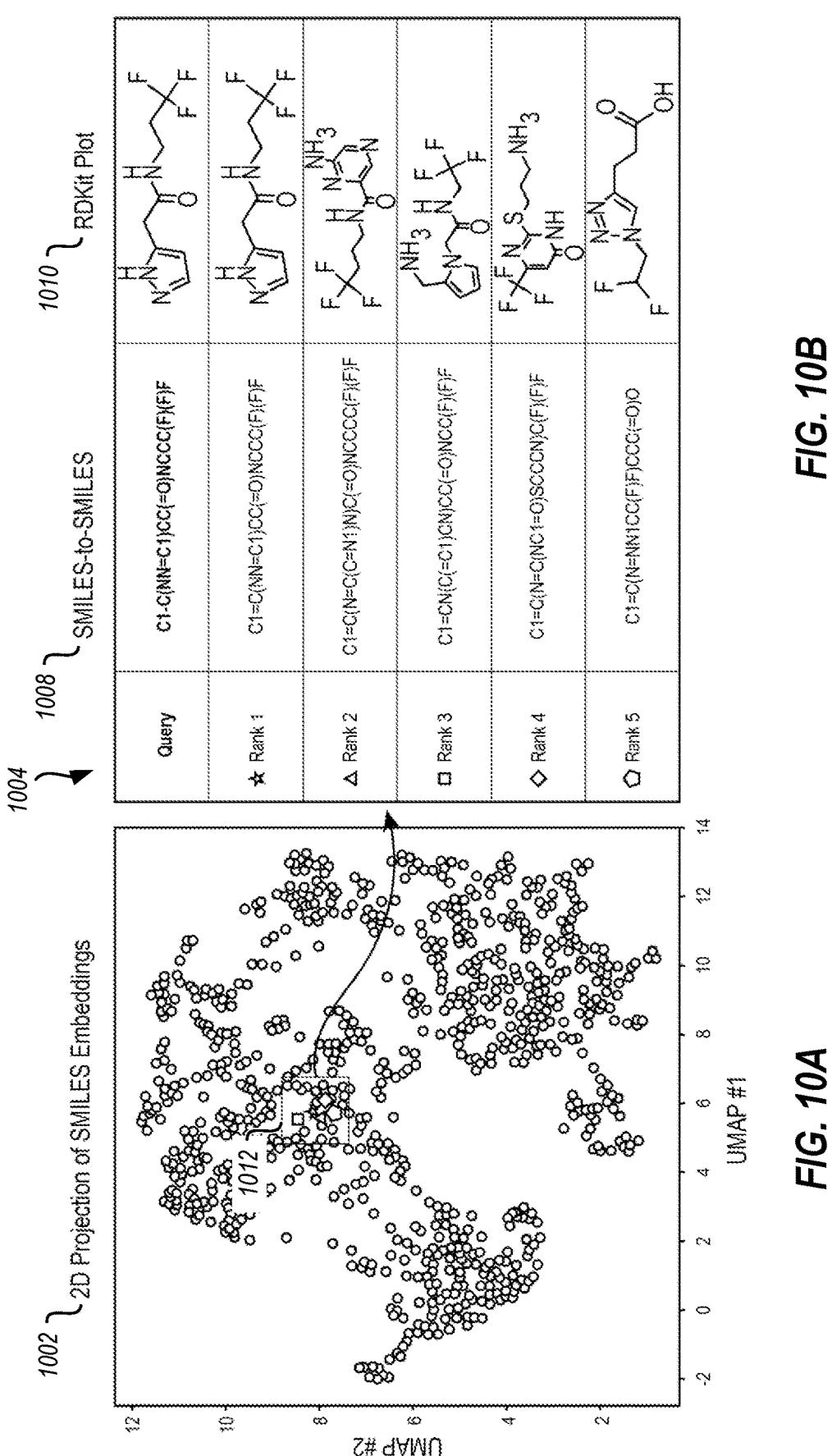
FIGS. 10A-10B illustrate an example embodiment of an output comprising unimodal entity-level retrieval results.

For example, FIGS. 10A-10B illustrate an example embodiment of an output comprising unimodal entity-level retrieval results. For example, FIGS. 10A-10B illustrates an example for SMILES-to-SMILES search across 100 k molecules. The left panel (FIG. 10A) shows a 2D projection 1002 of SMILES embeddings for the top 1 k ranked molecules based on the initial SMILES query. The right panel (FIG. 10B) is shown as a table 1004 comprising the example SMILES query 1006 and the top 5 ranked SMILES-to-Smiles strings 1008 (e.g., Rank 1, Rank 2, Rank 3, Rank 4, Rank 5). The RDKit plots 1010 of corresponding molecules are also placed next to each string for interpretation purpose. The locations of the top 5 molecules (represented by non-circular plot indicators) in the left panel are found to be near each other (i.e., within a limited region, as depicted by the black box 1012).

It should be appreciated that the results in FIGS. 10A-10B are representative of any unimodal entity-level retrieval results. For example, the model is able to perform IUPAC-to-IUPAC searches, as well as any other modality-to-modality searches for which the model is trained. Furthermore, any number of top results are plottable in the left panel, and any number of top results are retrievable, as shown in the right panel. In some embodiments, a user pre-determines the maximum number of molecules across which a query is searched, a maximum number of molecules that are plotted, and a maximum number of top entity-level results (as shown in the right panel). The results are also reported in various manners, including graphical, string-based, or other manner in which to represent the results to the user.

Figures 11A, 11B:
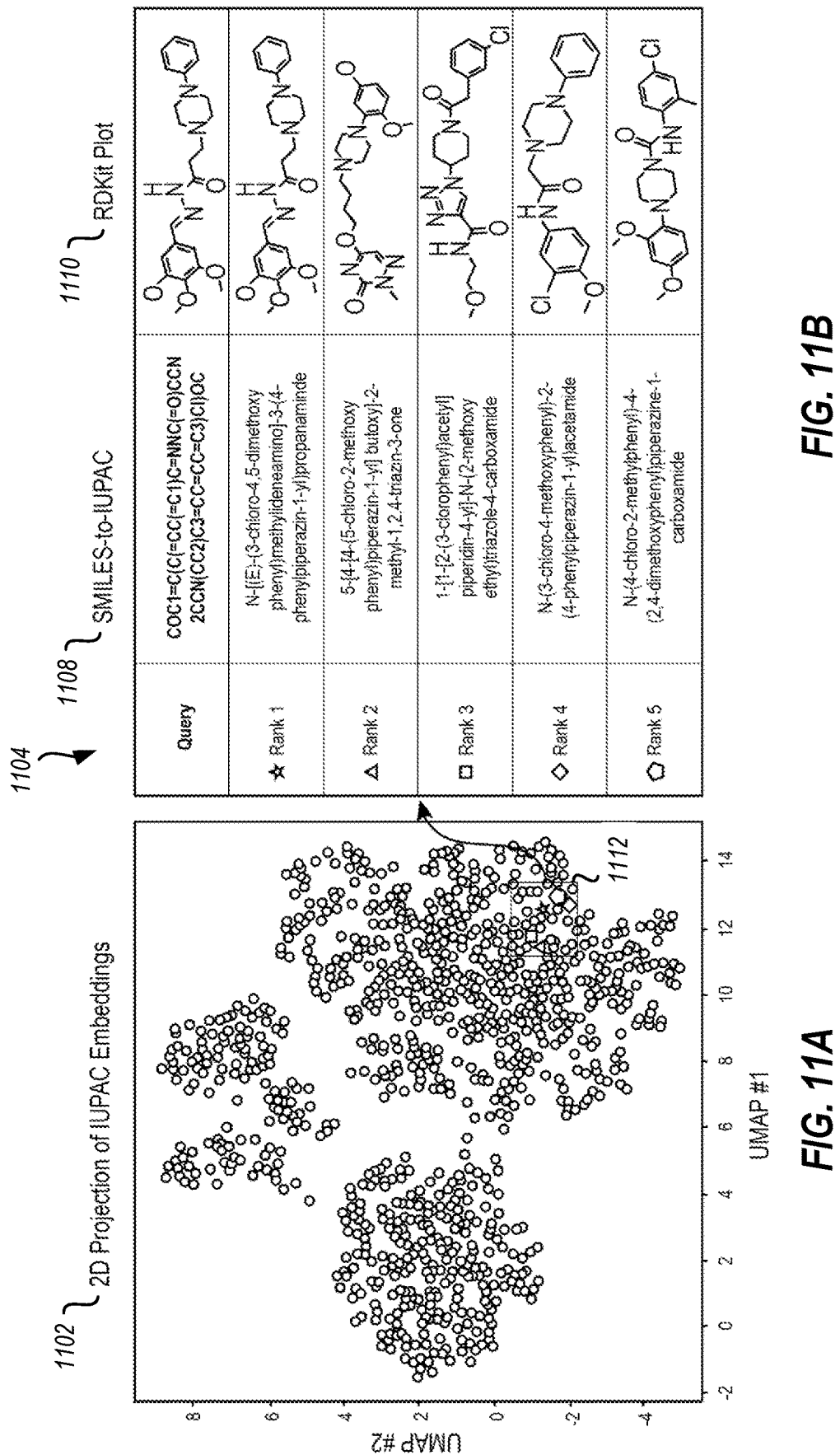
FIGS. 11A-11B illustrate an example embodiment of an output comprising multi-modal entity-level retrieval results.

Attention will now be directed to FIGS. 11A-11B, which illustrate an example embodiment of an output comprising multi-modal entity-level retrieval results. For example, SMILES-to-IUPAC search results are shown from a query across 100 k molecules. The left panel (FIG. 11A) shows a 2D projection 1102 of IUPAC embeddings for the top 1 k ranked molecules based on the SMILES-based query. The right panel (FIG. 11B) is configured as a table 1104 showing the example SMILES query 1106 and the top 5 ranked SMILES-to-IUPAC results 1108 (e.g., Rank 1, Rank 2, Rank 3, Rank 4, and Rank 5). RDKit plots 1110 of corresponding molecules are placed next to each string for interpretation purpose. The locations of the top 5 molecules are within a certain limited region size as shown by the black square 1112. This is representative of any number of top results being reported having similar embeddings (i.e., are positive pairs with short distances between embeddings). It should also be appreciated that the model is able to perform IUPAC-to-SMILES searches, in addition to any cross-modal searches that the model for which the model is trained.

When searching molecules across a plurality of molecules using cosine similarity, the embedding space is trained on particular set of molecules is observed to facilitate an improvement in performance in cross-modality searches. In addition, the model performs better when trained on larger datasets (e.g., ten million molecules vs. one million molecules). This shows that the model is scalable to very large datasets, even upwards to performing searches across one hundred million molecules. This greatly enhances search capacity and provides a great insight to molecular similarity between molecules. Furthermore, FIGS. 10A-11B show that the shared characteristics of the different examples of top retrieved results all have similar substructures with the initial query. The results also appear close in the embeddings pace. In unimodal searches, the sequences of the retrieved strings among the top results are more similar to each other than the sequences of retrieved strings for cross-modal searches, but both perform with accuracy that provides useful information informing a user about molecular similarity to the target molecule. The model is trained to maximize mutual information for pairs of modalities, not to encode the exact sequence of information of tokens for each modality in the embedding space. This allows the model to operate at a global molecule level, instead of a fragment level.

Figure 12:
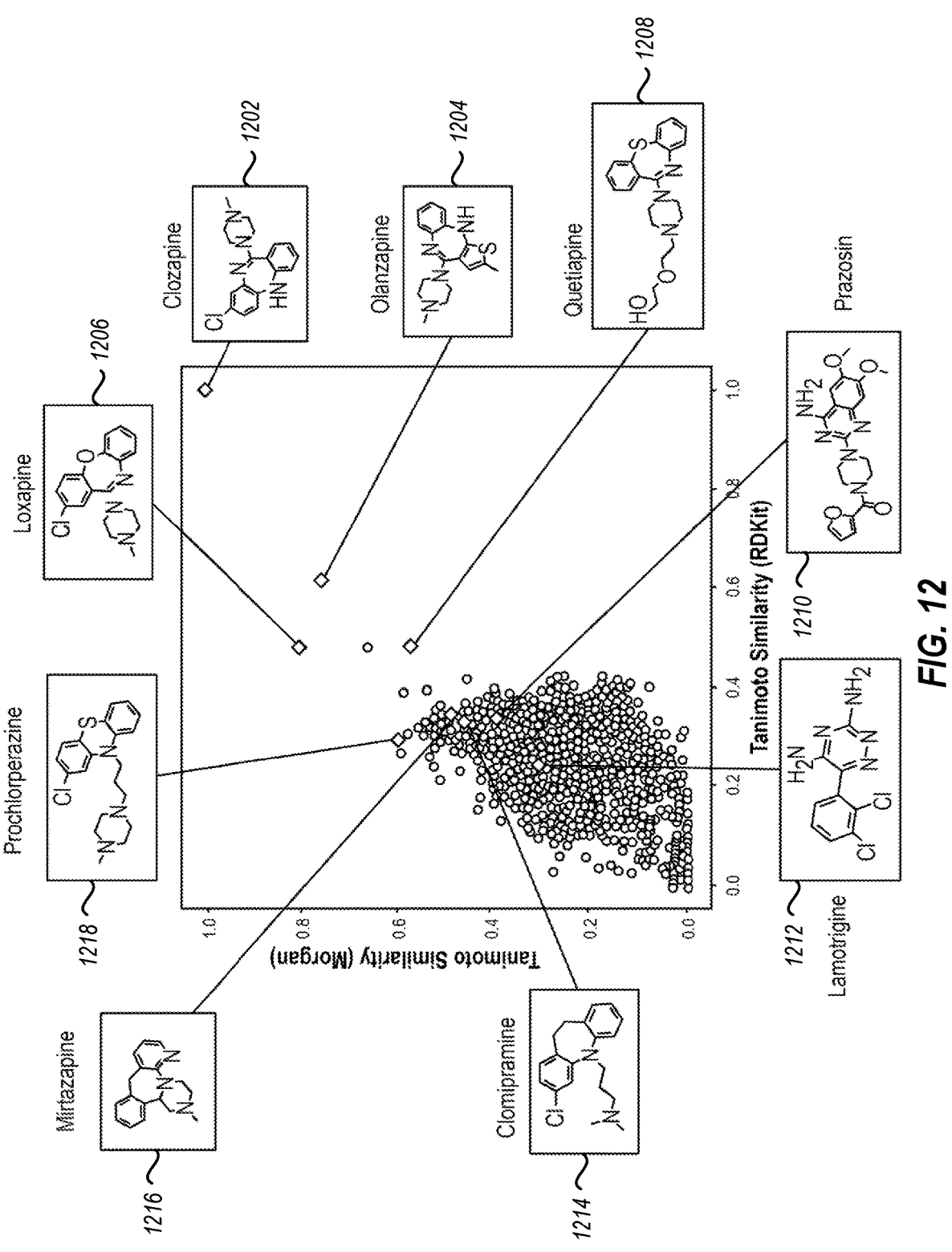
FIG. 12 illustrates an example embodiment of an output comprising drug similarity analysis and prediction.

Attention will now be directed to FIG. 12, which illustrates an example embodiment of an output comprising drug similarity analysis and prediction. For drug similarity assessment, a target drug is selected. The target drug shown in FIG. 12 is selected as Clozapine 1202. Besides cosine similarity, the system also computes other molecular similarity measurements, namely Tanimoto Similarity with RDKit fingerprint and Tanimoto Similarity with Morgan fingerprint, for comparison.

FIG. 12 show a scatter plot of various kinds of similarity scores between Clozapine and a plurality of other drugs. Top results are called out with the corresponding drug names and RDKit plot of the drug molecules. For example, Olanzapine 1204 and Loxapine 1206 are the most similar to Clozapine 1202. Quetiapine 1208 is also very similar to Clozapine 1202. Other drugs of interest include, Prazosin 1210, Lamotrigine 1212, Clomipramine 1214, Mirtazapine 1216, and Procholperazine 1218. In some embodiments, a threshold is defined for the similarity score in order for a drug to be designated as a drug of interest or predicted to be similar to the target drug.

Figure 13:
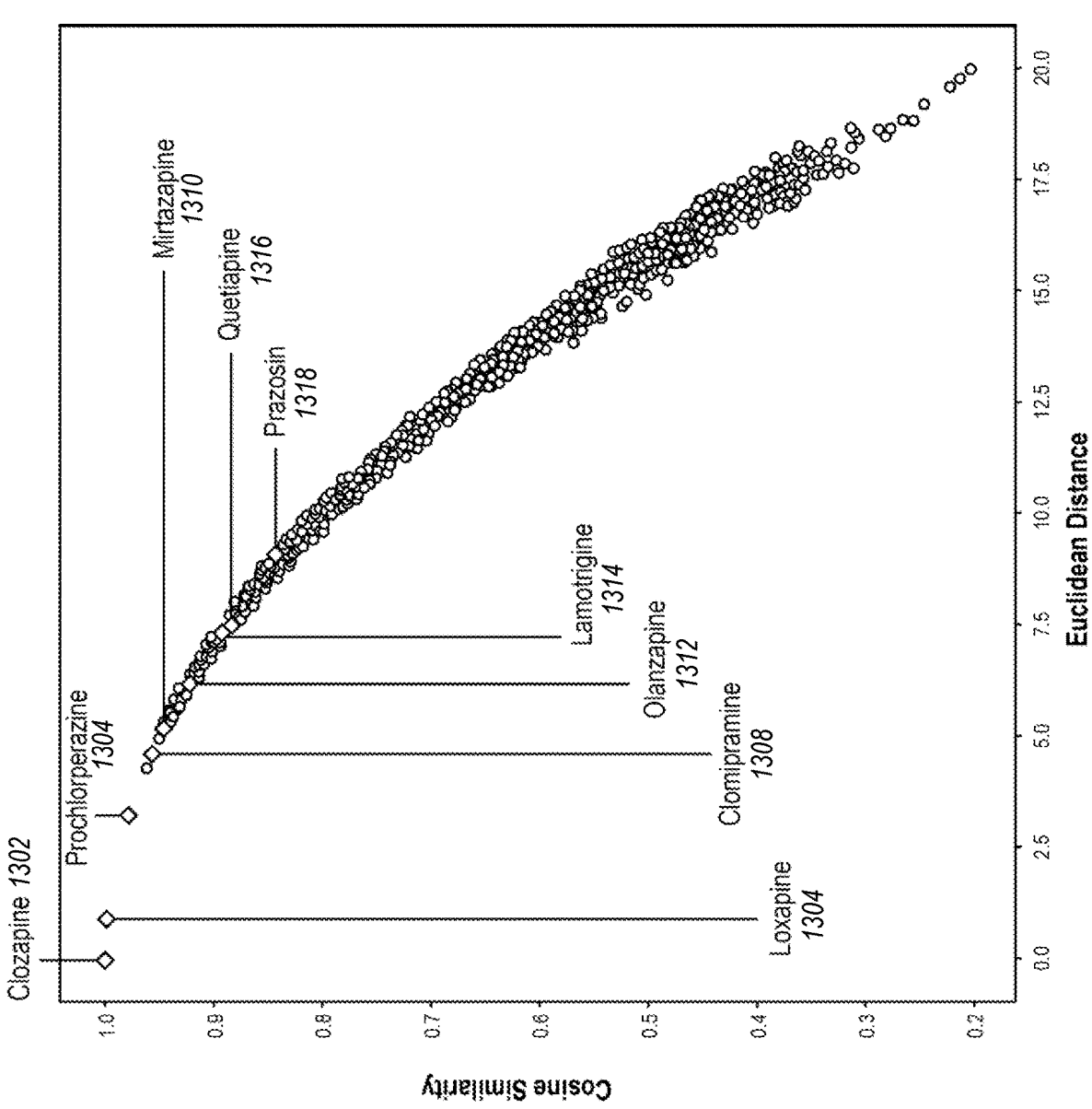
FIG. 13 illustrates another example embodiment of an output comprising drug similarity analysis and prediction.

Attention will now be direct to FIG. 13, which illustrates another example embodiment of an output comprising drug similarity analysis and prediction. FIG. 13 compares the cosine similarity with Euclidean distance. The Euclidean distance here measures the shortest distance between the Clozapine embedding with the embeddings of all drugs in an N-number (e.g., 512) dimensional space, whereas cosine similarity calculates the cosine of the angle between two embeddings. This figure compares the agreement of two different ways to measure closeness in the same space and the two measurements have a good alignment as shown in the plot. As shown in FIG. 13, the nearest drugs to Clozapine 1302, in descending similarity order are: Loxapine 1304, Procholperazine 1306, Clomipramine 1308, Mirtazapine 1310, Olanzapine 1312, Lamotrigine 1314, Quetiapine 1316, and Prazosin 1318. Thus, the model is shown to perform, wherein an equivalent set of similar drugs are returned for Clozapine 1302, with much high similarity scores than reference similarity scores (e.g., Tanimoto similarity scores), with Loxapine and Olanzapine being in the top 5 results for both FIG. 12 and FIG. 13.

When checking the similarity relationships of drugs with Clozapine (or another target drug) in a drug similarity assessment, the interested drugs have a similarity score above a particular threshold (e.g., 0.8). In addition, when comparing cosine similarity with Tanimoto similarity, there are some drugs that have a high cosine similarity score while a low Tanimoto similarity score (e.g., Proflavine). Like Clozapine, Proflavine have three fused rings, while the Tanimoto score is below 0.2 when using the RDKit fingerprint and Morgan fingerprint. Thus, it is shown that the cosine similarity score calculated by the model built and trained via methods and systems described herein beneficially provides an embedding space that has the ability to identify structural similarities beyond conventional methods (e.g., Tanimoto similarity). The embedding space also encodes structure similarities at the same time as encoding information of about the different functional groups identified in the various drugs/molecules.

When the model is also trained for drug-drug interaction, it is able to leverage information learned from molecular similarity searches and drug similarity assessments. The model is able to identify novel drug-drug interactions because of the structural and functional information that is encoded in the drug embeddings. Thus, the model (as trained in a self-supervised manner with cross-modal pairs) generates a molecular embedding space that fuses shared features between pairs of modalities and beneficially provides systems and methods for molecular representation in chemical and drug discoveries.

Figure 16:
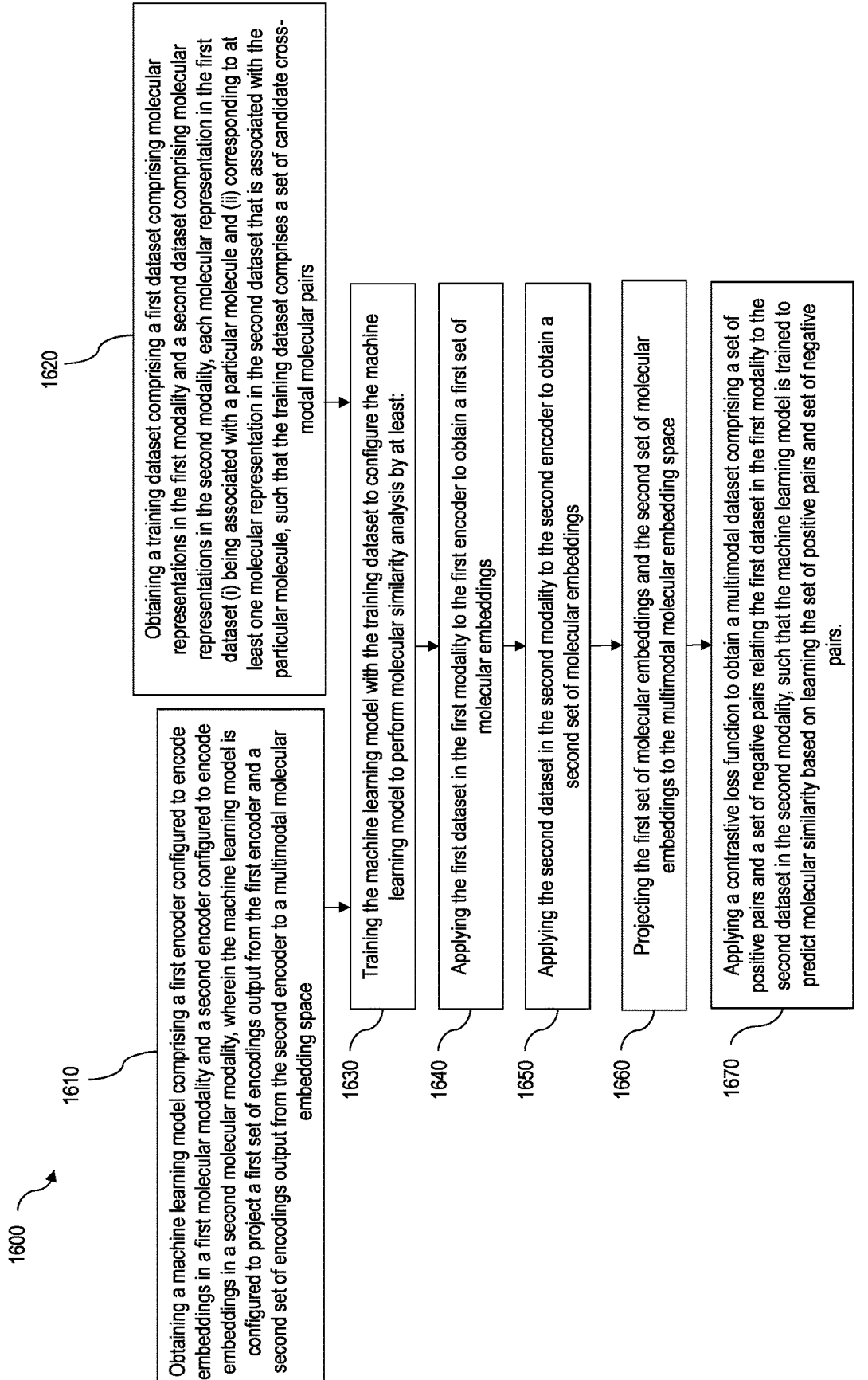
FIG. 16 illustrates a process flow diagram comprising a plurality of acts associated with a method for training and using a machine learning model configured to generate multimodal contrastive embeddings.

Attention will now be directed to FIGS. 14-16, which illustrates various example embodiments of methods for performing the disclosed embodiments. Although the method acts may be discussed in a certain order or illustrated in a flow chart as occurring in a particular order, no ordering is required unless specifically stated, or required because an act is dependent on another act being completed prior to the act being performed.

Attention will now be directed to FIG. 14, in some reference to FIG. 1, which illustrates a flow diagram 1400 that includes various acts (act 1410, act 1420, and act 1430) associated with exemplary methods that can be implemented by computing system 110 for building a machine learning model that is trainable to perform in-domain embedding analysis. As illustrated, the computing system first obtains a first encoder of the machine learning model trained to receive as input one or more entities represented in a first modality and encode the one or more entities in the first modality such that the first encoder is configured to output a first set of embeddings (act 1410).

The system also obtains a second encoder of the machine learning model trained to receive as input one or more entities represented in the second modality and encode the one or more entities in the second modality such that the second encoder is configured to output a second set of embeddings (act 1420). The system then configures a projection layer of the machine learning model to project the first set of embeddings and the second set of embeddings to a shared contrastive space (act 1430).

One or more computer-readable instructions are further executable to further configure the computing system to train a first tokenizer of the machine learning model to tokenize the one or more entities in the first modality into a first set of tokens prior to the first encoder receiving as input the one or more entities in the first modality, and train a second tokenizer of the machine learning model to tokenize the one or more entities in the second modality into a second set of tokens prior to the second encoder receiving as input the one or more entities in the second modality. The first encoder and second encoder are configured to receive the first and second sets of tokens at a global level.

To assist in facilitating the projection layer in projecting the embeddings to the embedding space, the system also configures a global average pooling layer of the machine learning model to integrate the first set of embeddings and second set of embeddings prior to the projection layer projecting the first set of embeddings and second set of embeddings to the shared contrastive space.

Attention will now be directed to FIG. 15, in some reference to FIG. 1, which illustrates a flow diagram 1500 that includes various acts (act 1510, act 1520, act 1530, act 1540, act 1550, act 1560, and act 1570) associated with exemplary methods that can be implemented by computing system 110 for training a machine learning model to perform in-domain embedding analysis. The system obtains a machine learning model comprising a first encoder trained to encode embeddings in a first modality and a second encoder trained to encode embeddings in a second modality (act 1510). The machine learning model is configured to project a first set of encodings output from the first encoder and a second set of encodings output from the second encoder to a shared contrastive embedding space.

The system also obtains a training dataset comprising a first dataset comprising data objects in the first modality and a second dataset comprising data objects in the second modality (act 1520). Each data object in the first dataset corresponds to a different data object in the second data set such that the training dataset comprises a set of candidate cross-modal pairs. The first dataset in the first modality is applied to the first encoder to obtain a first output (act 1530) and the second dataset in the second modality is applied to the second encoder to obtain a second output (act 1540).

Subsequently, the system projects the first output and the second output to the shared contrastive embedding space (act 1550) and applies a contrastive loss function to obtain a multi-modal dataset comprising a set of positive pairs and a set of negative pairs relating the first dataset in the first modality to the second dataset in the second modality (act 1560).

To perform unimodal embedding generation, the system applies a target entity in the first modality to the machine learning model to obtain a third output in the first modality.

To perform unimodal entity-level retrieval, the system applies the third output of a target entity in the first modality as a query to obtain entities predicted to be similar to the target entity. During the generation of unimodal clustering results, the third output of the entities in the first modality comprises a cluster map.

To perform unimodal cluster-level retrieval, one or more computer-readable instructions are further executable to further configure the computing system to identify hidden links among clusters included in the cluster map based on information obtained for a particular modality.

To perform cross-modal entity-level retrieval, the system obtains a third output of a target entity in the first modality to obtain one or more entities in the second modality that are predicted to be similar to the target entity.

To perform cross-modal cluster-level retrieval, the system applies entities in the first modality to the machine learning model to obtain third output in the first modality and entities in the second modality to the machine learning model to obtain fourth output in the second modality, wherein the third output comprises a cluster map in the first modality and the fourth output comprises a cluster map in the second modality. Links are identified between a particular cluster in the first modality to one or more clusters in the second modality based on a set of cluster properties extracted from the cluster map.

The model is also configured to generate cross-modal embeddings. For example, the system applies a target entity in the first modality and an entity corresponding to the target entity in the second modality at the same time to the machine learning model to obtain a fifth output configured as a general representation of the entity in a particular domain.

When the machine learning model is performing general embedding clustering, the fifth output comprises a cluster map of entities in a general representation space.

Attention will now be directed to FIG. 16, in some reference to FIG. 1, which illustrates a flow diagram 1600 that includes various acts (act 1610, act 1620, act 1630, act 1640, act 1650, act 1660, and act 1670) associated with exemplary methods that can be implemented by computing system 110 for training a machine learning model to perform in-domain embedding analysis for molecular embeddings, in particular for performing molecular similarity analysis. As illustrated, the system obtains a machine learning model comprising a first encoder configured to encode embeddings in a first molecular modality and a second encoder configured to encode embeddings in a second molecular modality (act 1610). The machine learning model is configured to project a first set of encodings output from the first encoder and a second set of encodings output from the second encoder to a multimodal molecular embedding space.

The system also obtains a training dataset comprising a first dataset comprising molecular representations in the first modality and a second dataset comprising molecular representations in the second modality (act 1620). Each molecular representation in the first dataset (i) is associated with a particular molecule and (ii) corresponds to at least one molecular representation in the second dataset that is associated with the particular molecule, such that the training dataset comprises a set of candidate cross-modal molecular pairs.

Subsequent to obtaining the training dataset, the system trains the machine learning model with the training dataset to configure the machine learning model to perform molecular similarity analysis (act 1630). The system trains the machine learning model by at least: applying the first dataset in the first modality to the first encoder to obtain a first set of molecular embeddings (act 1640), applying the second dataset in the second modality to the second encoder to obtain a second set of molecular embeddings (act 1650), projecting the first set of molecular embeddings and the second set of molecular embeddings to the multimodal molecular embedding space (act 1660), and applying a contrastive loss function to obtain a multimodal dataset comprising a set of positive pairs and a set of negative pairs relating the first dataset in the first modality to the second dataset in the second modality, such that the machine learning model is trained to predict molecular similarity based on learning the set of positive pairs and set of negative pairs (act 1670).

The machine learning model is able to be trained under various training techniques. In some instances, the training dataset is an unlabeled dataset such that the machine learning model is trained on the training dataset under self-supervision.

The model is trainable for many different types of modalities. In some instances, the first modality is SMILES and the second modality is IUPAC.

Where the model is performing molecular similarity analysis, the system receives a user input comprising a query to find one or more candidate molecules that are predicted to be similar to a target molecule and calculates one or more similarity score(s) between the target molecule and one or more candidate molecules. Based on the one or more similarity score(s), the system also determines a ranking of the one or more candidate molecules and returns a list of the one or more candidate molecules to the user. The list is organized according to the ranking.

In some instances, the target molecule and the one or more candidate molecules are represented in a same modality. Additionally, or alternatively, the target molecule is represented in the first modality and the one or more candidate molecules are represented in the second modality.

Prior to applying the first dataset in the first modality to the first encoder, the system tokenizes the first dataset to obtain a first set of token vectors associated with the first modality. Similarly, prior to applying the second dataset in the second modality to the second encoder, the system tokenizes the second dataset to obtain a second set of token vector associated with the second modality. The first set of token vectors is applied to the first encoder and the second set of token vectors is applied to the second encoder. Each set of token vectors being applied to its respective encoder at a global molecule level.

Where the machine learning model is configured to perform drug similarity analysis, the system receives a user input configured to query a database of drugs with a target drug and predicts that the target drug is similar to one or more drugs included in the database of drugs.

The machine learning model is also trainable to perform a drug interaction prediction. In such configurations, the system obtains a third training dataset comprising a plurality of known drug-drug interactions and trains the machine learning model with the third training dataset to configure the machine learning model to predict whether a first drug will interact with a second drug.

After training the machine learning model, the system receives a user input configured to query a target drug against a database of drugs and predicts that a target drug will have an interaction with one or more drugs included in the database of drugs.

In some embodiments, the system obtains a fourth dataset comprising a set of known molecular properties and trains the machine learning model with the fourth dataset to configure the machine learning model to predict a probability of a particular property being associated with a target drug.

In view of the foregoing, it will be appreciated that the disclosed embodiments provide many technical benefits over conventional systems and methods for building, training, and utilizing machine learning models for in-domain multi-modal embedding analysis.

Embodiments of the present invention may comprise or utilize a special purpose or general-purpose computer (e.g., computing system 110) including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system.

Computer-readable media (e.g., hardware storage device(s) 140 of FIG. 1) that store computer-executable instructions (e.g., computer-readable instructions 118 of FIG. 1) are physical hardware storage media/devices that exclude transmission media. Computer-readable media that carry computer-executable instructions or computer-readable instructions (e.g., computer-readable instructions 118) in one or more carrier waves or signals are transmission media. Thus, by way of example, and not limitation, embodiments of the invention can comprise at least two distinctly different kinds of computer-readable media: physical computer-readable storage media/devices and transmission computer-readable media.

Physical computer-readable storage media/devices are hardware and include RAM, ROM, EEPROM, CD-ROM or other optical disk storage (such as CDs, DVDs, etc.), magnetic disk storage or other magnetic storage devices, or any other hardware which can be used to store desired program code means in the form of computer-executable instructions or data structures and which can be accessed by a general purpose or special purpose computer.

A "network" (e.g., network 130 of FIG. 1) is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry, or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computing system configured to build a machine learning model that is trainable to perform in-domain embedding analysis, the computing system comprising:
   one or more processors; and
   one or more hardware storage devices storing one or more computer-readable instructions that are executable by the one or more processors to cause the computing system to:
   access a first encoder of the machine learning model;
   tokenize a first representation of an entity, resulting in generation of a first set of tokens for the entity, wherein the entity is represented in a first modality by the first representation;
   embed the first set of tokens into a first numeric matrix representation;
   generate a first positional encoding for the first set of tokens, wherein the first positional encoding preserves a first order of the tokens included in the first set of tokens;
   provide, to the first encoder, the first numeric matrix representation and the first positional encoding;
   cause the first encoder to encode the first numeric matrix representation and the first positional encoding, such that the first encoder is configured to output a first set of embeddings;
   access a second encoder of the machine learning model; trained to receive as input one or more entities represented in a second modality and
   tokenize a second representation of the entity, resulting in generation of a second set of tokens for the entity, wherein the entity is represented in a second modality by the second representation;
   embed the second set of tokens into a second numeric matrix representation;
   generate a second positional encoding for the second set of tokens, wherein the second positional encoding preserves a second order of the tokens included in the second set of tokens;
   provide, to the second encoder, the second numeric matrix representation and the second positional encoding;
   cause the second encoder to encode the second numeric matrix representation and the second positional encoding, such that the second encoder is configured to output a second set of embeddings; and
   configure a projection layer of the machine learning model to project the first set of embeddings and the second set of embeddings to a shared contrastive space.

2. The computing system of claim 1, the one or more computer-readable instructions being further executable to further configure the computing system to:
   configure a global average pooling layer of the machine learning model to integrate the first set of embeddings and second set of embeddings prior to the projection layer projecting the first set of embeddings and second set of embeddings to the shared contrastive space.

3. A method comprising:

accessing a first encoder of a machine learning model;

tokenizing a first representation of an entity, resulting in generation of a first set of tokens for the entity, wherein the entity is represented in a first modality by the first representation;

embedding the first set of tokens into a first numeric matrix representation;

generating a first positional encoding for the first set of tokens, wherein the first positional encoding preserves a first order of the tokens included in the first set of tokens;

providing, to the first encoder, the first numeric matrix representation and the first positional encoding;

causing the first encoder to encode the first numeric matrix representation and the first positional encoding, resulting in generation of a first set of encoded data;

accessing a second encoder of the machine learning model;

tokenizing a second representation of the entity, resulting in generation of a second set of tokens for the entity, wherein the entity is represented in a second modality by the second representation;

embedding the second set of tokens into a second numeric matrix representation;

generating a second positional encoding for the second set of tokens, wherein the second positional encoding preserves a second order of the tokens included in the second set of tokens;

providing, to the second encoder, the second numeric matrix representation and the second positional encoding;

causing the second encoder to encode the second numeric matrix representation and the second positional encoding, resulting in generation of a second set of encoded data; and configuring a projection layer of the machine learning model to project the first set of encoded data and the second set of encoded data to a shared contrastive space.

4. The method of claim 3, wherein the entity is related to a domain.

5. The method of claim 4, wherein the domain is a chemical domain.

6. The method of claim 4, wherein the domain is an enterprise domain.

7. The method of claim 3, wherein the first modality is an image modality.

8. The method of claim 7, wherein the second modality is an audio modality.

9. The method of claim 3, wherein the first modality is a text modality or an audio modality.

10. The method of claim 9, wherein the second modality is a different one of the text modality or the audio modality.

11. The method of claim 3, wherein at least one of the first or second encoders is configured as a plurality of transformer encoder blocks.

12. A computer system comprising:

one or more processors; and one or more hardware storage devices that store instructions that are executable by the one or more processors to cause the computer system to:

access a first encoder of a machine learning model;

tokenize a first representation of an entity, resulting in generation of a first set of tokens for the entity, wherein the entity is represented in a first modality by the first representation;

embed the first set of tokens into a first numeric matrix representation;

generate a first positional encoding for the first set of tokens, wherein the first positional encoding preserves a first order of the tokens included in the first set of tokens;

provide, to the first encoder, the first numeric matrix representation and the first positional encoding;

cause the first encoder to encode the first numeric matrix representation and the first positional encoding, resulting in generation of a first set of encoded data;

access a second encoder of the machine learning model;

tokenize a second representation of the entity, resulting in generation of a second set of tokens for the entity, wherein the entity is represented in a second modality by the second representation;

embed the second set of tokens into a second numeric matrix representation;

generate a second positional encoding for the second set of tokens, wherein the second positional encoding preserves a second order of the tokens included in the second set of tokens;

provide, to the second encoder, the second numeric matrix representation and the second positional encoding;

cause the second encoder to encode the second numeric matrix representation and the second positional encoding, resulting in generation of a second set of encoded data; and project the first set of encoded data and the second set of encoded data to a shared contrastive space.

13. The computer system of claim 12, wherein the entity is related to a domain.

14. The computer system of claim 13, wherein the domain is a chemical domain.

15. The computer system of claim 13, wherein the domain is an enterprise domain.

16. The computer system of claim 12, wherein the first modality is an image modality.

17. The computer system of claim 16, wherein the second modality is an audio modality.

18. The computer system of claim 12, wherein the first modality is one of an image modality, a text modality, or an audio modality.

19. The computer system of claim 18, wherein the second modality is a different one of the image modality, the text modality, or the audio modality.

20. The computer system of claim 12, wherein at least one of the first or second encoders is configured as a plurality of transformer encoder blocks.

* * * * *